(12) United States Patent
Leriche et al.

(10) Patent No.: US 8,546,575 B2
(45) Date of Patent: Oct. 1, 2013

(54) NIP THIAZOLE DERIVATIVES AS INHIBITORS OF 11-BETA-HYDROXYSTEROID DEHYDROGE-NASE-1

(75) Inventors: Caroline Leriche, Paris (FR); Denis Carniato, Marcoussis (FR); Didier Roche, Saclay (FR); Christine Charon, Gometz-le-Chatel (FR); Liliane Doare, Vitry-Chatillon (FR)

(73) Assignee: Merck Patent GmbH, Darmstadt (DE)

( * ) Notice: Subject to any disclaimer, the term of this patent is extended or adjusted under 35 U.S.C. 154(b) by 273 days.

(21) Appl. No.: 12/991,016

(22) PCT Filed: Apr. 8, 2009

(86) PCT No.: PCT/EP2009/002607
§ 371 (c)(1),
(2), (4) Date: Nov. 4, 2010

(87) PCT Pub. No.: WO2009/135581
PCT Pub. Date: Nov. 12, 2009

(65) Prior Publication Data
US 2011/0060007 A1    Mar. 10, 2011

(30) Foreign Application Priority Data
May 5, 2008  (EP) .................................... 08290424

(51) Int. Cl.
*C07D 215/00* (2006.01)
*A61K 31/47* (2006.01)

(52) U.S. Cl.
USPC .......................................... 546/164; 514/314

(58) Field of Classification Search
USPC .......................................................... 546/164
See application file for complete search history.

(56) References Cited

U.S. PATENT DOCUMENTS

| 2006/0069102 A1 | 3/2006 | Leban et al. |
| 2007/0231263 A1 | 10/2007 | Qiu et al. |
| 2010/0048583 A1 | 2/2010 | Leban et al. |

FOREIGN PATENT DOCUMENTS

| EP | 1 832 568 A1 | 9/2007 |
| WO | WO 2007/104557 A2 | 9/2007 |

OTHER PUBLICATIONS

International Search Report of PCT/EP2009/002607 (Feb. 8, 2010).

*Primary Examiner* — John Mabry
(74) *Attorney, Agent, or Firm* — Millen, White, Zelano & Branigan, P.C.

(57) ABSTRACT

The present invention relates to NIP thiazole derivatives of formula (I) as selective inhibitors of the enzyme 11-beta-hydroxysteroid dehydrogenase type 1 (11-β-HSD-1) and the use of such compounds for the treatment and prevention of metabolic syndrome, diabetes, insulin resistance, obesity, lipid disorders, glaucoma, osteoporosis, cognitive disorders, anxiety, depression, immune disorders, hypertension and other diseases and conditions.

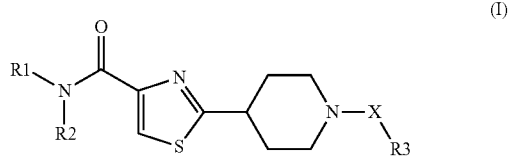

(I)

17 Claims, No Drawings

NIP THIAZOLE DERIVATIVES AS INHIBITORS OF 11-BETA-HYDROXYSTEROID DEHYDROGE-NASE-1

TECHNICAL FIELD

The present invention relates to Nip thiazoles derivatives as selective inhibitors of enzyme 11-beta-hydroxysteroid dehydrogenase type 1 (11-β-HSD-1) and the use of such compounds for the treatment and/or prevention of metabolic syndrome, diabetes, insulin resistance, obesity, lipid disorders, glaucoma, osteoporosis, cognitive disorders, anxiety, depression, immune disorders, hypertension and other diseases and conditions.

PRIOR ART

Hydroxysteroid dehydrogenases (HSDs) regulate the occupancy and activation of steroid hormone receptors by converting steroid hormones into their inactive metabolites. For a recent review, see Nobel et al., Eur. J. Biochem. 2001, 268: 4113-4125.

There exist numerous classes of HSDs. The 11-beta-hydroxysteroid de-hydrogenases (11-β-HSDs) catalyze the interconversion of active glucocorticoids (such as Cortisol and corticosterone), and their inert forms (such as cortisone and 11-dehydrocorticosterone). The isoform 11-beta-hydroxysteroid dehydrogenase type 1 (11-β-HSD-1) is widely expressed in liver, adipose tissue, brain, lung and other glucocorticoid tissue, while the isoform 2 (11-β-HSD-2) expression is limited to tissues that express the mineralocorticoid receptor, such as kidney, gut and placenta. Then the inhibition of 11β-HSD-2 is associated with serious side effects, such as hypertension.

Excess Cortisol is associated with numerous disorders, including diabetes, obesity, dyslipidemia, insulin resistance and hypertension. The administration of 11β-HSD-1 inhibitors decreases the level of Cortisol and other 11β-hydroxysteroids in target tissues, thereby reducing the effects of excessive amounts of Cortisol and other 11β-hydroxysteroids. Thus, 11-β-HSD-1 is a potential target for therapy associated with numerous disorders that may be ameliorated by reduction of glucocorticoid action. Therefore, the inhibition of 11-β-HSD-1 can be used to prevent, treat or control diseases mediated by abnormally high levels of Cortisol and other 11β-hydroxysteroids, such as diabetes, obesity, hypertension or dyslipidemia. Inhibition of 11-β-HSD-1 activity in the brain such as to lower Cortisol levels may also be useful to treat or reduce anxiety, depression, cognitive impairment or age-related cognitive dysfunction (Seckl, et al., Endocrinology, 2001, 142: 1371-1376).

Cortisol is an important and well recognized anti-inflammatory hormone, which also acts as an antagonist to the action of insulin in the liver, such that insulin sensitivity is reduced, resulting in increased gluconeogenesis and elevated levels of glucose in the liver. Patients who already have impaired glucose tolerance have a greater probability of developing type 2 diabetes in the presence of abnormally high levels of Cortisol (Long et al. J. Exp. Med, 1936, 63: 465-490; Houssay, Endocrinology 1942, 30: 884-892). In addition, it has been well substantiated that 11-β-HSD-1 plays an important role in the regulation of local glucocorticoid effect and of glucose production in the liver (Jamieson et al., J. Endocrinol. 2000, 165: 685-692). In Walker, et al., J. Clin. Endocrinol. Metab. 1995, 80: 3155-3159, it was reported that the administration of the non-specific 11β-HSD-1 inhibitor carbenoxolone resulted in improved hepatic insulin sensitivity in humans.

Furthermore, the hypothesized mechanism of action of 11-β-HSD-1 in the treatment of diabetes has been supported by various experiments conducted in mice and rats. These studies showed that the mRNA levels and activities of two key enzymes in hepatic glucose production, phosphoenolpyruvate carboxykinase (PEPCK) and glucose-6-phosphatase (G6Pase) were reduced upon administration of 11-β-HSD-1 inhibitors, in addition, blood glucose levels and hepatic glucose production were shown to be reduced in 11-β-HSD-1 knockout mice. Additional data gathered using this murine knockout model also confirm that inhibition of 11-β-HSD-1 will not cause hypoglycemia, since the basal levels of PEPCK and G6Pase are regulated independently of glucocorticoids (Kotelevtsev et al., Proc. Natl. Acad. Sci. USA 1997, 94: 14924-14929).

Therefore, the administration of a therapeutically effective amount of an 11-β-HSD-1 inhibitor is effective in treating, controlling and ameliorating the symptoms of diabetes, especially non-insulin dependent diabetes (NIDDM, type 2 diabetes mellitus) and administration of a therapeutically effective amount of an 11-β-HSD-1 inhibitor on a regular basis delays or prevents the onset of diabetes, particularly in humans.

The effect of elevated levels of Cortisol is also observed in patients who have Cushing's Syndrome, which is a metabolic disease characterized by high levels of Cortisol in the blood stream. Patients with Cushing's Syndrome often develop NIDDM.

Excessive levels of Cortisol have been associated with obesity, perhaps due to increased hepatic gluconeogenesis. Abdominal obesity is closely associated with glucose intolerance, diabetes, hyperinsulinemia, hypertriglyceridemia and other factors of Metabolic Syndrome, such as high blood pressure, elevated VLDL and reduced HDL (Montague et al., Diabetes, 2000, 49: 883-888). In obese subjects, 11-β-HSD-1 activity in adipose tissue is markedly increased and positively correlated with body mass, it has also been reported that inhibition of the 11-β-HSD-1 in pre-adipocytes (stromal cells) resulted in a decreased rate of differentiation into adipocytes. This is predicted to result in diminished expansion (possibly reduction) of the omental fat depot, which may lead to reduced central obesity (Bujaiska et al., Lancet 1997, 349: 1210-1213).

Thus, the administration of an effective amount of an 11-β-HSD-1 inhibitor is useful in the treatment or control of obesity. Long-term treatment with an 11-β-HSD-1 inhibitor is also useful in delaying or preventing the onset of obesity, especially if the patient uses an 11-β-HSD-1 inhibitor in combination with controlled diet end exercise.

By reducing insulin resistance and maintaining serum glucose at normal concentrations, compounds of the present invention also have utility in the treatment and prevention of conditions that accompany type 2 diabetes and insulin resistance, including the Metabolic Syndrome, obesity, reactive hypoglycemia and diabetic dyslipidemia.

Inhibition of 11-β-HSD-1 in mature adipocytes is expected to attenuate secretion of the plasminogen activator inhibitor 1 (PA1-1), which is an independent cardiovascular risk factor, as reported in Halleux et al., J; Clin. Endocrinol. Metab. 1999, 84: 4097-4105. In addition, a correlation has been shown to exist between glucocorticoid activity and certain cardiovascular risk factors. This suggests that a reduction of the glucocorticoid effects would be beneficial in the treatment or prevention of certain cardiovascular diseases (Walker et al., Hypertension 1998, 31: 891-895; and Fraser et al., Hypertension 1999, 33: 1364 1368).

Since hypertension and dyslipidemia contribute to the development of atherosclerosis and inhibition of 11-β-HSD-1 activity and a reduction in the amount of Cortisol are beneficial in treating or controlling hypertension, administration of a therapeutically effective amount of an 11-β-HSD-1 inhibitor of the present invention may also be especially beneficial in treating, controlling or delaying the onset of or preventing atherosclerosis.

11-β-HSD-1 has also been implicated in the process of appetite control and therefore is believed to play an additional role in weight-related disorders. It is known that adrenalectomy attenuates the effect of fasting to increase both food intake and hypothalamic neuropeptide Y expression. This suggests that glucocorticoids play a role in promoting food intake and that inhibition of 11-β-HSD-1 in the brain may increase satiety, thus resulting in a decreased food intake (Woods et al., Science 1998, 280: 1378-1383).

Another possible therapeutic effect associated with modulation of 11-β-HSD-1 is that which is related to various pancreatic aliments. It is reported that inhibition of 11β-HSD-1 in murine pancreatic β-cells increases glucose stimulated insulin secretion (Davani et al., J. Biol. Chem. 2000, 275: 34841-34844). This follows from the preceding discovery that glucocorticoids were previously found to be responsible for reduced pancreatic insulin release in vivo (Billaudel et al., Horm. Metab. Res. 1979, 11: 555-560). Thus, it is suggested that inhibition of 11-β-HSD-1 would yield other beneficial effects in the treatment of diabetes other than the predicted effects on the liver and of fat reduction.

Excessive levels of Cortisol in the brain may also result in neuronal loss or dysfunction through the potentiation of neurotoxins. Administration of an effective amount of an 11-β-HSD-1 inhibitor results in the reduction, amelioration, control or prevention of cognitive impairment associated with aging and of neuronal dysfunction. Cognitive impairment has been associated with aging, and excess levels of Cortisol in the brain (see J. R. Seeckl and B. R. Walker, Endocrinology, 2001, 142: 1371 1376, and references cited therein). 11β-HSD-1 also regulates glucocorticoid activity in the brain and thus contributes to neurotoxicity (Rajan et al., Neuroscience 1996, 16: 65-70; Seckl et al., Necroendocrinol. 2000, 18: 49-99). Stress and/or glucocorticoids are known to influence cognitive function (de Quervain et al., Nature 1998, 394: 787-790), and unpublished results indicate significant memory improvement in rats treated with a non-specific 11β-HSD-1 inhibitor. These reports, in addition to the known effects of glucocorticoids in the brain, suggest that inhibiting 11β-HSD-1 in the brain may have a positive therapeutic effect against anxiety, depression and related conditions (Tranche et al., Nature Genetics 1999, 23: 99-103). 11β-HSD-1 reactivates 11-dehydrocorticosterone to corticosterone in hippocampal cells and can potentiate kinase neurotoxicity, resulting in age-related learning impairments. Therefore, selective inhibitors of 11β-HSD-1 are believed to protect against hippocampal function decline with age (Yau et al., Proc Natl. Acad. Sci. USA 2001, 98: 4716-4721). Thus, it has been hypothesized that inhibition of 11β-HSD-1 in the human brain would protect against deleterious glucocorticoid-mediated effects on neuronal function, such as cognitive impairment, depression, and increased appetite.

Furthermore, 11β-HSD-1 is believed to play a role in immunomodulation based on the general perception that glucocorticoids suppress the immune system. There is known to be a dynamic interaction between the immune system and the HPA (hypothalamic-pituitary-adrenal) axis (Rook, Baillier's Clin. Endocrinol. Metab. 2000, 13: 576-581), and glucocorticoids help balance between cell-mediated responses and humoral responses.

Increased glucocorticoid activity, which may be induced by stress, is associated with a humoral response and as such, the inhibition of 11β-HSD-1 may result in shifting the response towards a cell-based reaction. In certain disease states, such as tuberculosis, leprosy and psoriasis, and even under conditions of excessive stress, high glucocorticoid activity shifts the immune response to a humoral response, when in fact a cell based response may be more beneficial to the patient. Inhibition of 11β-HSD-1 activity and the attendant reduction in glucocorticoid levels on the other hand shifts the immune response toward a cell based response (D. Mason, Immunology Today, 1991, 12: 57-60, and G. A. Vt. Rook, Baillier's Clin. Endocrinol. Metab., 1999, 13: 576-581). It follows then, that an alternative utility of 11β-HSD-1 inhibition would be to bolster a temporal immune response in association with immunization to ensure that a cell based response would be obtained.

Recent reports suggest that the levels of glucocorticoid target receptors and of HSDs are connected with the susceptibility to glaucoma (J. Stokes et al., Invest. Ophthalmol. 2000, 41: 1629-1638). Further, a connection between inhibition of 11β-HSD-1 and a lowering of the intraocular pressure was recently reported (Walker et al., poster P3-698 at the Endocrine society meeting Jun. 12-15, 1999, San Diego), it was shown that administration of the nonspecific 11β-HSD-1 inhibitor carbenoxolone resulted in the reduction of the intraocular pressure by 20% in normal patients. In the eye, 11β-HSD-1 is expressed exclusively in the basal cells of the corneal epithelium, the non-pigmented epithelium of the cornea (the site of aqueous production), ciliary muscle, and the sphincter and dilator muscles of the iris. In contrast, the distant isoenzyme 11-hydroxysteroid dehydrogenase type 2 ("11-β-HSD-2") is highly expressed in the non-pigmented ciliary epithelium and corneal endothelium. No HSDs have been found at the trabecular meshwork, which is the site of drainage. Therefore, 11-β-HSD-1 is suggested to have a role in aqueous production and inhibition of 11-β-HSD-1 activity is useful in reducing intraocular pressure in the treatment of glaucoma.

Glucocorticoids also play an essential role in skeletal development and function but are detrimental to such development and function when present in excess. Glucocorticoid-induced bone loss is partially derived from suppression of osteoblast proliferation and collagen synthesis, as reported in C. H. Kim et al., J. Endocrinol. 1999, 162: 371 379. It has been reported that the detrimental effects of glucocorticoids on bone nodule formation can be lessened by administration of carbenoxolone, which is a non-specific 11-β-HSD-1 inhibitor (C. G. Bellows et al., Bone 1998, 23: 119-125). Additional reports suggest that 11-β-HSD-1 maybe responsible for providing increased levels of active glucocorticoid in osteoclasts, and thus in augmenting bone resorption (M. S. Cooper et al., Bone 2000, 27: 375-381). This data suggests that inhibition of 11-β-HSD-1 may have beneficial effects against osteoporosis via one or more mechanisms which may act in parallel.

11-β-HSD-1 inhibitors are known e.g. from the WO 04/10629, WO 03/065983, WO 04/089896, WO 04/089380, WO 04/065351, WO 04/033427 or WO 04/041264. For a recent review see M. Wamil and J. R. Seckl (Drug Discovery Today; June 2007, page 504-520) and C. D. Boyle, T. J. Kowalski and L. Zhang (Annual reports in medicinal chemistry; 2006, 41, 127-140). However, Nip thiazoles are not disclosed as active 11-β-HSD-1 inhibitors.

Thiazoles derivatives are disclosed for example in WO 2007/11805, WO 2007/123269, WO 2007/104557, WO 2007/104558, EP 1 832 586, WO 2007/014290, WO 2007/016979, WO 2006/032322, WO 2005/116653, WO 2005/074934, WO 2004/058751, WO 2004/058750, WO 2004/041815, WO 2001/74788, WO 97/15567, WO 2005/113522, US 2005/0250784, US 2005/0234033, WO 2005/049018, WO 02/088093, WO 98/46599, WO 98/28282, WO 96/25414, US 2006/247253, US 2006/069102, FR 2865733, FR 2856685, Leban J et al., (Bioorg Med Chem Let 2007, 17: 5858-5862) and Xing L et al., (J Comp Molec Design 2004, 18: 333-344).

The disclosure of these publications, however, does not encompass the Nip thiazoles derivatives of the present invention nor the use of the disclosed compounds as 11-β-HSD-1 inhibitors.

The citation of any reference in this application is not an admission that the reference is prior art to this application.

DESCRIPTION OF THE INVENTION

The present invention has the object to provide novel thiazole derivatives that act as 11-β-HSD-1 inhibitors.

The object of the present invention has surprisingly been solved in one aspect by providing the use of a thiazole derivative according to formula (I)

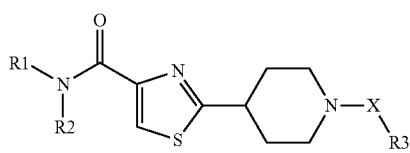

(I)

wherein:
R1, R2 are independently from each other alkyl, cycloalkyl or heterocyclyl, wherein the alkyl, cycloalkyl or heterocyclyl is optionally substituted by at./ least one substituent selected from alkyl, cycloalkyl or hydroxyl, or R1, R2 and the nitrogen to which they are attached form a saturated mono- or bicyclic ring containing 3-20, preferably 6-10 atoms, optionally containing at least one further heteroatom selected from N, S or O and optionally being substituted by at least one substituent selected from halogen, alkyl, hydroxyl, =O (carbonyl oxygen), aryl or heteroaryl;
R3 is alkyl, cycloalkyl, cycloalkyl-alkyl, aryl, aryl-alkyl, heteroaryl or heteroaryl-alkyl, wherein alkyl, cycloalkyl, cycloalkyl-alkyl, aryl, aryl-alkyl, heteroaryl or heteroaryl-alkyl is optionally substituted by at least one substituent selected from halogen, hydroxyl, C(O)OH, CN, C(O)—NH2, carbamoyl, acetamide, alkyl, aryl, phenyl, methoxy-phenyl, fluorophenyl, phenoxy, aryloxy, alkyloxy, $C_1$-$C_4$-alkyloxy, methoxy, trifluoromethyl, trifluoromethoxy, trifluoromethylthio, alkyloxycarbonyl, $C_1$-$C_4$-alkyloxycarbonyl, alkylcarbonyl, $C_1$$C_4$-alkylcarbonyl, R4R5N$C_1$-$C_4$-alkyloxy, or $C_1$-$C_4$-alkyl-S(O)$_n$, wherein n is 0, 1 or 2;
R4, R5 are independently from each other alkyl or cycloalkyl;
X is a direct bond, C(O), C(O)O, S(O)$_2$ or C(O)NH;
and the physiologically acceptable salts, derivatives, prodrugs, solvates and stereoisomers thereof, including mixtures thereof in all ratios,
as 11-β-HSD-1 inhibitor.

In a preferred embodiment, the use of thiazole derivatives according to formula (I) as 11-β-HSD-1 inhibitor is provided, wherein
R1, R2 are independently from each other alkyl or cycloalkyl optionally substituted by at least one substituent selected from alkyl, cycloalkyl or hydroxyl,
and the physiologically acceptable salts, derivatives, prodrugs, solvates and stereoisomers thereof, including mixtures thereof in all ratios.

In a preferred embodiment, the use of thiazole derivatives according to formula (I) as 11-β-HSD-1 inhibitor is provided, wherein
R1, R2 are independently from each other methyl, cyclopropyl or cyclohexyl, optionally substituted by at least one substituent selected from alkyl, cycloalkyl or hydroxyl,
and the physiologically acceptable salts, derivatives, prodrugs, solvates and stereoisomers thereof, including mixtures thereof in all ratios.

In a preferred embodiment, the use of thiazole derivatives according to formula (I) as 11-β-HSD-1 inhibitor is provided, wherein
R1, R2 and the nitrogen to which they are attached form a saturated mono- or bicyclic ring containing 6-10 atoms, optionally being substituted by at least one substituent selected from halogen, alkyl, hydroxyl, =O (carbonyl oxygen), aryl or heteroaryl.
and the physiologically acceptable salts, derivatives, prodrugs, solvates and stereoisomers thereof, including mixtures thereof in all ratios.

In a preferred embodiment, the use of thiazole derivatives according to formula (I) as 11-β-HSD-1 inhibitor is provided, wherein
R1, R2 and the nitrogen to which they are attached form piperidine or octahydroquinoline, optionally being substituted by at least one substituent selected from halogen, alkyl, hydroxyl, =O (carbonyl oxygen), aryl or heteroaryl.
and the physiologically acceptable salts, derivatives, prodrugs, solvates and stereoisomers thereof, including mixtures thereof in all ratios.

In a preferred embodiment, the use of thiazole derivatives according to formula (I) as 11-β-HSD-1 inhibitor is provided, wherein
X is a direct bond;
R3 is alkyl, cycloalkyl-alkyl or heterocyclyl-alkyl, optionally substituted by at least one substituent selected from halogen, hydroxyl, C(O)OH, CN, C(O)—NH$_2$, carbamoyl, acetamide, alkyl, aryl, phenyl, methoxy-phenyl, fluoro-phenyl, phenoxy, aryloxy, alkyloxy, $C_1$-$C_4$-alkyloxy, methoxy, trifluoromethyl, trifluoromethoxy, trifluoromethylthio, alkyloxycarbonyl, $C_1$-$C_4$-alkyloxycarbonyl, alkylcarbonyl, $C_1$-$C_4$-alkylcarbonyl, R4R5N$C_1$-$C_4$-alkyloxy, or $C_1$-$C_4$-alkyl-S(O)$_n$, wherein n is 0, 1 or 2.
and the physiologically acceptable salts, derivatives, prodrugs, solvates and stereoisomers thereof, including mixtures thereof in all ratios.

In a preferred embodiment, the use of thiazole derivatives according to formula (I) as 11-β-HSD-1 inhibitor is provided, wherein
X is a direct bond;
R3 is cyclohexyl-methyl, cyclohexyl-ethyl, tetrahydropyryl-methyl, cyano-methyl, pentyl, isobutyl, butyl, methyl-butyl or aminocarbonyl-methyl.

and the physiologically acceptable salts, derivatives, prodrugs, solvates and stereoisomers thereof, including mixtures thereof in all ratios.

In a preferred embodiment, the use of thiazole derivatives according to formula (I) as 11-β-HSD-1 inhibitor is provided, wherein X is C(O) or C(O)O;

R3 is alkyl, cycloalkyl, aryl or heteroaryl, optionally substituted by at least one substituent selected from halogen, hydroxyl, C(O)OH, CN, C(O)—NH$_2$, carbamoyl, acetamide, alkyl, aryl, phenyl, methoxy-phenyl, fluorophenyl, phenoxy, aryloxy, alkyloxy, $C_1$-$C_4$-alkyloxy, methoxy, trifluoromethyl, trifluoromethoxy, trifluoromethylthio, alkyloxycarbonyl, $C_1$-$C_4$-alkyloxycarbonyl, alkylcarbonyl, $C_1$-$C_4$-alkylcarbonyl, R4R5NC$_1$-$C_4$-alkyloxy, or $C_1$-$C_4$-alkyl-S(O)$_n$, wherein n is 0, 1 or 2.

and the physiologically acceptable salts, derivatives, prodrugs, solvates and stereoisomers thereof, including mixtures thereof in all ratios.

In a preferred embodiment, the use of thiazole derivatives according to formula (I) as 11-β-HSD-1 inhibitor is provided, wherein X is C(O) or C(O)O;

R3 is methyl, ethyl, propyl, dimethyl-propyl, butyl, pentyl, tert. butyl, cyclopropyl, cyclobutyl, cyclopentyl, cyclohexyl, phenyl or pyridinyl, optionally substituted by at least one substituent selected from halogen, hydroxyl, C(O)OH, CN, C(O)—NH$_2$, carbamoyl, acetamide, alkyl, aryl, phenyl, methoxy-phenyl, fluorophenyl, phenoxy, aryloxy, alkyloxy, $C_1$-$C_4$-alkyloxy, methoxy, trifluoromethyl, trifluoromethoxy, trifluoromethylthio, alkyloxycarbonyl, $C_1$-$C_4$-alkyloxycarbonyl, alkylcarbonyl, $C_1$-$C_4$-alkylcarbonyl, R4R5NC$_1$-$C_4$-alkyloxy, or $C_1$-$C_4$-alkyl-S(O)$_n$, wherein n is 0, 1 or 2.

and the physiologically acceptable salts, derivatives, prodrugs, solvates and stereoisomers thereof, including mixtures thereof in all ratios.

In a preferred embodiment, the use of thiazole derivatives according to formula (I) as 11-β-HSD-1 inhibitor is provided, wherein X is C(O)NH;

R3 is alkyl or cycloalkyl, optionally substituted by at least one substituent selected from halogen, hydroxyl, C(O)OH, CN, C(O)—NH$_2$, carbamoyl, acetamide, alkyl, aryl, phenyl, methoxy-phenyl, fluorophenyl, phenoxy, aryloxy, alkyloxy, $C_1$-$C_4$-alkyloxy, methoxy, trifluoromethyl, trifluoromethoxy, trifluoromethylthio, alkyloxycarbonyl, $C_1$-$C_4$-alkyloxycarbonyl, alkylcarbonyl, $C_1$-$C_4$-alkylcarbonyl, R4R5NC$_1$-$C_4$-alkyloxy, or $C_1$-$C_4$-alkyl-S(O)$_n$, wherein n is 0, 1 or 2.

and the physiologically acceptable salts, derivatives, prodrugs, solvates and stereoisomers thereof, including mixtures thereof in all ratios.

In a preferred embodiment, the use of thiazole derivatives according to formula (I) as 11-β-HSD-1 inhibitor is provided, wherein X is C(O)NH;

R3 is ethyl, propyl, isopropyl, butyl, pentyl or cyclopentyl.

and the physiologically acceptable salts, derivatives, prodrugs, solvates and stereoisomers thereof, including mixtures thereof in all ratios.

In a preferred embodiment, the use of thiazole derivatives according to formula (I) as 11-β-HSD-1 inhibitor is provided, wherein X is S(O)$_2$;

R3 is alkyl, aryl, heteroaryl, aryl-alkyl or heteroaryl-alkyl, optionally substituted by at least one substituent selected from halogen, hydroxyl, C(O)OH, CN, C(O)—NH$_2$, carbamoyl, acetamide, alkyl, aryl, phenyl, methoxyphenyl, fluorophenyl, phenoxy, aryloxy, alkyloxy, $C_1$-$C_4$-alkyloxy, methoxy, trifluoro-methyl, trifluoromethoxy, trifluoromethylthio, alkyloxycarbonyl, $C_1$-$C_4$-alkyloxycarbonyl, alkylcarbonyl, $C_1$-$C_4$-alkylcarbonyl, R4R5NC$_1$-$C_4$-alkyloxy, or $C_1$-$C_4$-alkyl-S(O)$_n$, wherein n is 0, 1 or 2.

and the physiologically acceptable salts, derivatives, prodrugs, solvates and stereoisomers thereof, including mixtures thereof in all ratios.

In a preferred embodiment, the use of thiazole derivatives according to formula (I) as 11-β-HSD-1 inhibitor is provided, wherein X is S(O)$_2$;

R3 is methyl, ethyl, propyl, butyl, phenyl-methyl, pyridinyl-ethyl or thiophenyl, optionally substituted by at least one substituent selected from halogen, hydroxyl, C(O)OH, CN, C(O)—NH$_2$, carbamoyl, acetamide, alkyl, aryl, phenyl, methoxy-phenyl, fluorophenyl, phenoxy, aryloxy, alkyloxy, $C_1$-$C_4$-alkyloxy, methoxy, trifluoromethyl, trifluoromethoxy, trifluoromethylthio, alkyloxycarbonyl, $C_1$-$C_4$-alkyloxycarbonyl, alkylcarbonyl, $C_1$-$C_4$-alkylcarbonyl, R4R5NC$_1$-$C_4$-alkyloxy, or $C_1$-$C_4$-alkyl-S(O)$_n$, wherein n is 0, 1 or 2.

and the physiologically acceptable salts, derivatives, prodrugs, solvates and stereoisomers thereof, including mixtures thereof in all ratios.

In a preferred embodiment, thiazole derivatives according to formula (I) and above preferred embodiments and their use as 11-β-HSD-1 inhibitors are provided that are selected from the group consisting of:

a) 3,3-Dimethyl-1-{4-[4-(octahydro-quinoline-1-carbonyl)-thiazol-2-yl]-piperidin-1-yl}-butan-1-one
b) (Octahydro-quinolin-1-yl)-{2-[1-(pyridine-3-carbonyl)-piperidin-4-yl]-thiazol-4-yl}-methanone
c) 2-(1-Cyclohexanecarbonyl-piperidin-4-yl)-thiazole-4-carboxylic acid cyclohexyl-cyclopropyl-amide
d) 2-(1-Cyclopentanecarbonyl-piperidin-4-yl)-thiazole-4-carboxylic acid cyclohexyl-cyclopropyl-amide
e) 2-(1-Cyclobutanecarbonyl-piperidin-4-yl)-thiazole-4-carboxylic acid cyclohexyl-cyclopropyl-amide
f) 2-(1-Cyclopropanecarbonyl-piperidin-4-yl)-thiazole-4-carboxylic acid cyclohexyl-cyclopropyl-amide
g) 2-[1-(3-Cyclopentyl-propionyl)-piperidin-4-yl]-thiazole-4-carboxylic acid cyclohexyl-cyclopropyl-amide
h) 2-[1-(2-Ethyl-butyryl)-piperidin-4-yl]-thiazole-4-carboxylic acid cyclohexyl-cyclopropyl-amide
i) 2-[1-(3,3-Dimethyl-butyryl)-piperidin-4-yl]-thiazole-4-carboxylic acid cyclohexyl-cyclopropyl-amide
j) 2-[1-(3-Methyl-butyryl)-piperidin-4-yl]-thiazole-4-carboxylic acid cyclo-hexyl-cyclopropyl-amide
k) 2-(1-Isobutyryl-piperidin-4-yl)-thiazole-4-carboxylic acid cyclohexyl-cyclopropyl-amide
l) 2-(1-Pentanoyl-piperidin-4-yl)-thiazole-4-carboxylic acid cyclohexyl-cyclopropyl-amide
m) 2-(1-Propionyl-piperidin-4-yl)-thiazole-4-carboxylic acid cyclohexyl-cyclopropyl-amide
n) 2-(1-Acetyl-piperidin-4-yl)-thiazole-4-carboxylic acid cyclohexyl-cyclopropyl-amide
o) 2-[1-(Pyridine-3-carbonyl)-piperidin-4-yl]-thiazole-4-carboxylic acid cyclohexyl-cyclopropyl-amide
p) 2-[1-(4-Trifluoromethoxy-benzoyl)-piperidin-4-yl]-thiazole-4-carboxylic acid cyclohexyl-cyclopropyl-amide
q) [2-(1-Cyclohexanecarbonyl-piperidin-4-yl)-thiazol-4-yl]-(octahydro-quinolin-1-yl)-methanone r) [2-(1-Cyclopentanecarbonyl-piperidin-4-yl)-thiazol-4-yl]-(octahydro-quinolin-1-yl)-methanone
s) [2-(1-Cyclobutanecarbonyl-piperidin-4-yl)-thiazol-4-yl]-(octahydro-quinolin-1-yl)-methanone
t) [2-(1-Cyclopropanecarbonyl-piperidin-4-yl)-thiazol-4-yl]-(octahydro-quinolin-1-yl)-methanone
u) 3-Cyclopentyl-1-{4-[4-(octahydro-quinoline-1-carbonyl)-thiazol-2-yl]-piperidin-1-yl}-propan-1-one
v) 2-Ethyl-1-{4-[4-(octahydro-quinoline-1-carbonyl)-thiazol-2-yl]-piperidin-1-yl}-butan-1-one
w) 3-Methyl-1-{4-[4-(octahydro-quinoline-1-carbonyl)-thiazol-2-yl]-pipendin-1-yl}-butan-1-one
x) 2-Methyl-1-{4-[4-(octahydro-quinoline-1-carbonyl)-thiazol-2-yl]-piperidin-1-yl}-propan-1-one
y) 1-{4-[4-(Octahydro-quinoline-1-carbonyl)-thiazol-2-yl]-piperidin-1-yl}-pentan-1-one
z) 1-{4-[4-(Octahydro-quinoline-1-carbonyl)-thiazol-2-yl]-piperidin-1-yl}-propan-1-one
aa) 1-{4-[4-(Octahydro-quinoline-1-carbonyl)-thiazol-2-yl]-piperidin-1-yl}-ethanone
bb) (Octahydro-quinolin-1-yl)-{2-[1-(4-trifluoromethoxy-benzoyl)-piperidin-4-yl]-thiazol-4-yl}-methanone
cc) {2-[1-(4-Fluoro-benzoyl)-piperidin-4-yl]-thiazol-4-yl}-(octahydro-quinolin-1-yl)-methanone
dd) {2-[1-(4-Fluoro-benzoyl)-piperidin-4-yl]-thiazol-4-yl}-(4-hydroxy-octahydro-quinolin-1-yl)-methanone
ee) 1-{4-[4-(4-Hydroxy-octahydro-quinoline-1-carbonyl)-thiazol-2-yl]-piperidin-1-yl}-2-(4-methoxy-phenyl)-ethanone
ff) 4-[4-(4-Hydroxy-octahydro-quinoine-1-carbonyl)-thiazol-2-yl]-piperidine-1-carboxylic acid tert-butyl ester
gg) 2-[1-(2-Phenyl-butyryl-piperidin-4-yl]-thiazole-4-carboxylic acid cyclo-hexyl-cyclopropyl-amide
hh) 2-{1-[2-(4-Methoxy-phenyl)-acetyl]-piperidin-4-yl}-thiazole-4-carboxylic acid cyclohexyl-cyclopropyl-amide
ii) 2-[1-(2-Phenoxy-acetyl)-piperidin-4-yl]-thiazole-4-carboxylic acid cyclo-hexyl-cyclopropyl-amide
jj) 4-[4-(Cyclohexyl-cyclopropyl-carbamoyl)-thiazol-2-yl]-piperidine-1-carboxylic acid tert-butyl ester
kk) 1-{4-[4-(Octahydro-quinoline-1-carbonyl)-thiazol-2-yl]-piperidin-1-yl}-2-phenyl-butan-1-one
ll) 2-(4-Methoxy-phenyl)-1-{4-[4-(octahydro-quinoline-1-carbonyl)-thiazol-2-yl]-piperidin-1-yl}-ethanone,
mm) 1-{4-[4-(Octahydro-quinoline-1-carbonyl)-thiazol-2-yl]-piperidin-1-yl}-2-phenoxy-ethanone
nn) 4-[4-(Octahydro-quinoline-1-carbonyl)-thiazol-2-yl]-piperidine-1-carboxylic acid tert-butyl ester
oo) 2-Phenyl-1-{4-[4-(piperidine-1-carbonyl)-thiazol-2-yl]-piperidin-1-yl}-butan-1-one
pp) 2-(4-Methoxy-phenyl)-1-{4-[4-(piperidine-1-carbonyl)-thiazol-2-yl]-piperidin-1-yl}-ethanone
qq) 2-Phenoxy-1-{4-[4-(piperidine-1-carbonyl)-thiazol-2-yl]-piperidin-1-yl}-ethanone
rr) 4-[4-(Piperidine-1-carbonyl)-thiazol-2-yl]-piperidine-1-carboxylic acid tert-butyl ester
ss) 2-[1-(2-Phenyl-butyryl)-piperidin-4-yl]-thiazole-4-carboxylic acid cyclo-hexyl-methyl-amide
tt) 2-{1-[2-(4-Methoxy-phenyl)-acetyl]-piperidin-4-yl}-thiazole-4-carboxylic acid cyclohexyl-methyl-amide
uu) 2-[1-(2-Phenoxy-acetyl)-piperidin-4-yl]-thiazole-4-carboxylic acid cyclo-hexyl-methyl-amide
vv) 4-[4-(Octahydro-quinoline-1-carbonyl)-thiazol-2-yl]-piperidine-1-carboxylic acid sec-butylamide
ww) 4-[4-(Octahydro-quinoline-1-carbonyl)-thiazol-2-yl]-piperidine-1-carboxylic acid tert-butylamide
xx) 4-[4-(Octahydro-quinoline-1-carbonyl)-thiazol-2-yl]-piperidine-1-carboxylic acid propylamide
yy) 4-[4-(Octahydro-quinoline-1-carbonyl)-thiazol-2-yl]-piperidine-1-carboxylic acid ethylamide
zz) 4-[4-(Octahydro-quinoline-1-carbonyl)-thiazol-2-yl]-piperidine-1-carboxylic acid cyclopentylamide
aaa) 4-[4-(Octahydro-quinoline-1-carbonyl)-thiazol-2-yl]-piperidine-1-carboxylic acid isopropylamide
bbb) 4-[4-(Octahydro-quinoline-1-carbonyl)-thiazol-2-yl]-piperidine-1-carboxylic acid pentylamide
ccc) 4-[4-(Cyclohexyl-cyclopropyl-carbamoyl)-thiazol-2-yl]-piperidine-1-carboxylic acid sec-butylamide
ddd) 4-[4-(Cyclohexyl-cyclopropyl-carbamoyl)-thiazol-2-yl]-piperidine-1-carboxylic acid tert-butylamide
eee) 4-[4-(Cyclohexyl-cyclopropyl-carbamoyl)-thiazol-2-yl]-piperidine-1-carboxylic acid propylamide
fff) 4-[4-(Cyclohexyl-cyclopropyl-carbamoyl)-thiazol-2-yl]-piperidine-1-carboxylic acid ethylamide
ggg) 4-[4-(Cyclohexyl-cyclopropyl-carbamoyl)-thiazol-2-yl]-piperidine-1-carboxylic acid cyclopentylamide
hhh) 4-[4-(Cyclohexyl-cyclopropyl-carbamoyl)-thiazol-2-yl]-piperidine-1-carboxylic acid isopropylamide
iii) 4-[4-(Cyclohexyl-cyclopropyl-carbamoyl)-thiazol-2-yl]-piperidine-1-carboxylic acid pentylamide
jjj) 4-[4-(4-Hydroxy-octahydro-quinoline-1-carbonyl)-thiazol-2-yl]-piperidine-1-carboxylic acid 4-methoxy-benzylamide
kkk) 4-[4-(4-Hydroxy-octahydro-quinoline-1-carbonyl)-thiazol-2-yl]-piperidine-1-carboxylic acid (4-butyl-phenyl)-amide
lll) 3-({4-[4-(Cyclohexyl-cyclopropyl-carbamoyl)-thiazol-2-yl]-piperidine-1-carbonyl}-amino)-propionic acid
mmm) 4-[4-(Cyclohexyl-cyclopropyl-carbamoyl)-thiazol-2-yl]-piperidine-1-carboxylic acid (4-butyl-phenyl)-amide
nnn) 4-[4-(Cyclohexyl-cyclopropyl-carbamoyl)-thiazol-2-yl]-piperidine-1-carboxylic acid 4-methoxy-benzylamide
ooo) 3-({4-[4-(Octahydro-quinoline-1-carbonyl)-thiazol-2-yl]-piperidine-1-carbonyl}-amino)-propionic acid
ppp) 4-[4-(Octahydro-quinoline-1-carbonyl)-thiazol-2-yl]-piperidine-1-carboxylic acid (4-butyl-phenyl)-amide
qqq) 4-[4-(Octahydro-quinoline-1-carbonyl)-thiazol-2-yl]-piperidine-1-carboxylic acid 4-methoxy-benzylamide
rrr) 3-({4-[4-(Piperidine-1-carbonyl)-thiazol-2-yl]-piperidine-1-carbonyl}-amino)-propionic acid
sss) 4-[4-(Piperidine-1-carbonyl)-thiazol-2-yl]-piperidine-1-carboxylic acid (4-butyl-phenyl)-amide
ttt) 4-[4-(Piperidine-1-carbonyl)-thiazol-2-yl]-piperidine-1-carboxylic acid 4-methoxy-benzylamide
uuu) 3-({4-[4-(Cyclohexyl-methyl-carbamoyl)-thiazol-2-yl]-piperidine-1-carbonyl}-amino)-propionic acid
vvv) 4-[4-(Cyclohexyl-methyl-carbamyl)-thiazol-2-yl]-piperidine-1-carboxylic acid (4-butyl-phenyl)-amide
www) 4-[4-(Cyclohexyl-methyl-carbamoyl)-thiazol-2-yl]-piperidine-1-carboxylic acid 4-methoxy-benzylamide
xxx) (Octahydro-quinolin-1-yl)-[2-(1-trifluoromethane-sulfonyl-piperidin-4-yl)-thiazol-4-yl]-methanone
yyy) {2-[1-(Butane-1-sulfonyl)-piperidin-4-yl]-thiazol-4-yl}-(octahydro-quinolin-1-yl)-methanone zzz) (Octahydro-quinolin-1-yl)-{2-[1-(propane-1-sulfonyl)-peridin-4-yl]-thiazol-4-yl}-methanone
aaaa) [2-(1-Ethanesulfonyl-pipendin-4-yl)-thiazol-4yl]-(octahydro-quinolin-1-yl)-methanone
bbbb) 2-(1-Trifluoromethanesulfonyl-piperidin-4-yl)-thiazole-4-carboxylic acid cyclohexyl-cyclopropyl-amide
cccc) 2-[1-(Butane-1-sulfonyl)-piperidin-4-yl]-thiazole-4-carboxylic acid cyclohexyl-cyclopropyl-amide
dddd) 2-[1-(Propane-2-sulfonyl)-piperidin-4-yl]-thiazole-4-carboxylic acid cyclohexyl-cyclopropyl-amide
eeee) 2-[1-(Propane-1-sulfonyl)-piperidin-4-yl]-thiazole-4-carboxylic acid cyclohexyl-cyclopropyl-amide
ffff) 2-(1-Ethanesulfonyl-piperidin-4-yl)-thiazole-4-carboxylic acid cyclo-hexyl-cyclopropyl-amide
gggg) (Octahydro-quinolin-1-yl)-{2-[1-(thiophene-2-sulfonyl)-piperidin-4-yl]-thiazol-4-yl}-methanone
hhhh) 2-[1-(Thiophene-2-sulfonyl)-piperidin-4-yl]-thiazole-4-carboxylic acid cyclohexyl-cyclopropyl-amide
iiii) 2-[1-(4-Trifluoromethoxy-benzenesulfonyl)-piperidin-4-yl]-thiazole-4-carboxylic acid cyclohexyl-cyclopropyl-amide
jjjj) 2-[1-(4-Fluoro-benzenesulfonyl)-piperidin-4-yl]-thiazole-4-carboxylic acid cyclohexyl-cyclopropyl-amide
kkkk) (Octahydro-quinolin-1-yl)-{2-[1-(4-trifluoromethoxy-benzenesulfonyl)-piperidin-4-yl]-thiazol-4-yl}-methanone
llll) {2-[1-(4-Fluoro-benzenesulfonyl)-piperidin-4-yl]-thiazol-4-yl}-(octahydro-quinolin-1-yl)-methanone
mmmm) {2-[1-(4-Fluoro-benzenesulfonyl)-piperidin-4-yl]-thiazol-4-yl}-(4-hydroxy-octahydro-quinolin-1-yl)-methanone
nnnn) (4-Hydroxy-octahydro-quinolin-1-yl)-[2-(1-methanesulfonyl-piperidin-4-yl)-thiazol-4-yl]-methanone
oooo) 2-[1-(2-Pyridin-4-yl-ethanesulfonyl)-piperidin-4-yl]-thiazole-4-carboxylic acid cyclohexyl-cyclopropyl-amide
pppp) Piperidin-1-yl-{2-[1-(2-pyridin-4-y!-ethanesulfonyl)-piperidin-4-yl]-thiazol-4-yl}-methanone
qqqq) 2-[1-(4-Methoxy-benzenesulfonyl)-piperidin-4-yl]-thiazole-4-carboxylic acid cyclohexyl-cyclopropyl-amide
rrrr) 2-[1-(4-tert-Butyl-benzenesulfonyl)-piperidin-4-yl]-thiazole-4-carboxylic acid cyclohexyl-cyclopropyl-amide
ssss) 2-(1-Methanesulfonyl-piperidin-4-yl)-thiazole-4-carboxylic acid cyclohexyl-cyclopropyl-amide
tttt) {2-[1-(4-Methoxy-benzenesulfonyl)-piperidin-4-yl]-thiazol-4-yl}-(octahydro-quinolin-1-yl)-methanone
uuuu) {2- [1-(4-tert-Butyl-benzenesulfonyl)-piperidin-4-yl]-thiazol-4-yl}-(octahydro-quinolin-1-yl)-methanone
vvvv) [2-(1-Methanesulfonyl-piperidin-4-yl)-thiazol-4-yl]-(octahydro-quinolin-1-yl)-methanone
wwww) {2-[1-(4-Methoxy-benzenesulfonyl)-piperidin-4-yl]-thiazol-4-yl}-piperidin-1-yl-methanone
xxxx) {2-[1-(4-tert-Butyl-benzenesulfonyl)-piperidin-4-yl]-thiazol-4-yl}-piperidin-1-yl-methanone
yyyy) [2-(1-Methanesulfonyl-piperidin-4-yl)-thiazol-4-yl]-piperidin-1-yl-methanone
zzzz) 2-[1-(4-Methoxy-benzenesulfonyl)-piperidin-4-yl]-thiazole-4-carboxylic acid cyclohexyl-methyl-amide
aaaaa) 2-[1-(4-tert-Butyl-benzenesulfonyl)-piperidin-4-yl]-thiazole-4-carboxylic acid cyclohexyl-methyl-amide
bbbbb) 2-(1-Methanesulfonyl-piperidin-4-yl)-thiazole-4-carboxylic acid cyclohexyl-methyl-amide
ccccc) 2-(1-Cyclohexylmethyl-piperidin-4-yl)-thiazole-4-carboxylic acid cyclohexyl-cyclopropyl-amide
ddddd) [2-(1-Cyclohexylmethyl-piperidin-4-yl)-thiazol-4-yl]-(octahydro-quinolin-1-yl)-methanone
eeeee) 2-[1-(2-Cyclohexyl-ethyl)-piperidin-4-yl]-thiazole-4-carboxylic acid cyclohexyl-cyclopropyl-amide
fffff) 2-[1-(Tetrahydro-pyran-2-ylmethyl)-piperidin-4-yl]-thiazole-4-carboxylic acid cyclohexyl-cyclopropyl-amide
ggggg) 2-(1-Cyanomethyl-piperidin-4-yl)-thiazole-4-carboxylic acid cyclo-hexyl-cyclopropyl-amide
hhhhh) 2-(1-Carbamoylmethyl-piperidin-4-yl)-thiazole-4-carboxylic acid cyclohexyl-cyclopropyl-amide
iiiii) 2-(1-Pentyl-piperidin-4-yl)-thiazole-4-carboxylic acid cyclohexyl-cyclopropyl-amide
jjjjj) 2-(1-Isobutyl-piperidin-4-yl)-thiazole-4-carboxylic acid cyclohexyl-cyclopropyl-amide
kkkkk) 2-[1-(3-Methyl-butyl)-piperidin-4-yl]-thiazole-4-carboxylic acid cyclohexyl-cyclopropyl-amide
lllll) 2-(1-Butyl-piperidin-4-yl)-thiazole-4-carboxylic acid cyclohexyl-cyclopropyl-amide
mmmmm) {2-[1-(2-Cyclohexyl-ethyl)-piperidin-4-yl]-thiazol-4-yl}-(octahydro-quinolin-1-yl)-methanone
nnnnn) (Octahydro-quinolin-1-yl)-{2-[1-(tetrahydro-pyran-2-ylmethyl)-piperidin-4-yl]-thiazol-4-yl}-methanone
ooooo) {4-[4-(Octahydro-quinoline-1-carbonyl)-thiazol-2-yl]-piperidin-1-yl}-acetonitrile
ppppp) 2-{4-[4-(Octahydro-quinoline-1-carbonyl)-thiazol-2-yl]-piperidin-1-yl}-acetamide
qqqqq) (Octahydro-quinolin-1-yl)-[2-(1-pentyl-piperidin-4-yl)-thiazol-4-yl]-methanone
rrrrr) [2-(1-Isobutyl-piperidin-4-yl)-thiazol-4-yl]-(octahydro-quinolin-1-yl)-methanone
sssss) {2-[1-(3-Methyl-butyl)-piperidin-4-yl]-thiazol-4-yl}-(octahydro-quinolin-1-yl)-methanone
ttttt) [2-(1-Butyl-piperidin-4-yl)-thiazol-4-yl]-(octahydro-quinolin-1-yl)-methanone and the physiologically acceptable salts, derivatives, prodrugs, solvates and stereoisomers thereof, including mixtures thereof in ail ratios.

All the above generically or explicitly disclosed thiazole derivatives, including preferred subsets/embodiments of formula (I) and Compounds a) to ttttt), are hereinafter referred to as compounds of the (present) invention.

The nomenclature as used herein for defining compounds, especially the compounds according to the invention, is in general based on the rules of the IUPAC-organisation for chemical compounds and especially organic compounds.

The terms indicated for explanation of the above compounds of the invention always, unless indicated otherwise in the description or in the claims, have the following meanings:

The term "unsubstituted" means that the corresponding radical, group or moiety has no substituents.

The term "substituted" means that the corresponding radical, group or moiety has one or more substituents. Where a radical has a plurality of substituents, and a selection of various substituents is specified, the substituents are selected independently of one another and do not need to be identical.

The terms "alkyl" or "A" as well as other groups having the prefix "alk" for the purposes of this invention refer to acyclic saturated or unsaturated hydrocarbon radicals which may be branched or straight-chain and preferably have 1 to 8 carbon atoms, i.e. $C_1$-$C_8$-alkanyls, $C_2$-$C_8$-alkenyls and $C_2$-$C_8$-alkynyls. Alkenyls have at least one C-C double bond and alkynyls at least one C-C triple bond. Alkynyls may additionally also have at least one C-C double bond. Examples of suitable alkyl radicals are methyl, ethyl, n-propyl, isopropyl, n-butyl, isobutyl, sec-butyl, tert-butyl, n-pentyl, iso-pentyl, neo-pentyl, tert-pentyl, 2- or 3-methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl, ethylenyl (vinyl), propenyl ($-CH_2CH=CH_2$; $-CH=CH-CH_3$, $-C(=CH_2)-CH_3$), butenyl, pentenyl, hexenyl, heptenyl, octenyl, octadienyl, octadecenyl, octadec-9-enyl, icosenyl, icos-11-enyl, (Z)-icos-11-enyl, docosnyl, docos-13-enyl, (Z)-docos-13-enyl, ethynyl, propynyl ($-CH_2-C\equiv CH$, $-C\equiv C-CH_3$), butynyl, pentynyl, hexynyl, heptynyl, octynyl. Especially preferred is $C_{1-4}$-alkyl. A $C_{1-4}$-alkyl radical is for example a methyl, ethyl, propyl, isopropyl, butyl, isobutyl, tert-butyl.

The term "cycloalkyl" for the purposes of this invention refers to saturated and partially unsaturated non-aromatic cyclic hydrocarbon groups/radicals, having 1 to 3 rings, that contain 3 to 20, preferably 3 to 12, most preferably 3 to 8 carbon atoms. The cycloalkyl radical may also be part of a bi- or poly-cyclic system, where, for example, the cycloalkyl radical is fused to an aryl, heteroaryl or heterocyclyl radical as defined herein by any possible and desired ring member(s). The bonding to the compounds of the general formula (I) can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl. Especially preferred are $C_3$-$C_9$-cycloalkyl and $C_4$-$C_8$-cycloalkyl. A $C_4$-$C_8$-cycloalkyl radical is for example a cyclobutyl, cyclopentyl, cyclohexyl, cycloheptyl, cyclooctyl.

The term "heterocyclyl" for the purposes of this invention refers to a mono- or polycyclic system of 3 to 20, preferably 5 or 6 to 14 ring atoms comprising carbon atoms and 1, 2, 3, 4, or 5 heteroatoms, in particular nitrogen, oxygen and/or sulfur which are identical or different. The cyclic system may be saturated, mono- or polyunsaturated but may not be aromatic. In the case of a cyclic system consisting of at least two rings the rings may be fused or spiro- or otherwise connected. Such "heterocyclyl" radicals can be linked via any ring member. The term "heterocyclyl" also includes systems in which the heterocycle is part of a bi- or polycyclic saturated, partially unsaturated and/or aromatic system, such as where the heterocycle is fused to an "aryl", "cycloalkyl", "heteroaryl" or "heterocyclyl" group as defined herein via any desired and possible ring member of the heterocycyl radical. The bonding to the compounds of the general formula (I) can be effected via any possible ring member of the heterocycyl radical. Examples of suitable "heterocyclyl" radicals are pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetra-hydropyranyl, morpholinyl, tetrahydrothiophenyl, dihydropyranyl.

The term "aryl" for the purposes of this invention refers to a mono- or polycyclic aromatic hydrocarbon systems having 3 to 14, preferably 5 to 14, more preferably 6 to 10 carbon atoms. The term "aryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the aryl radical. The bonding to the compounds of the general formula (I) can be effected via any possible ring member of the aryl radical. Examples of suitable "aryl" radicals are phenyl, biphenyl, naphthyl, 1-naphthyl, 2-naphthyl and anthracenyl, but likewise indanyl, indenyl, or 1,2,3,4-tetrahydronaphthyl. The most preferred aryl is phenyl.

The term "heteroaryl" for the purposes of this invention refers to a 3 to 15, preferably 5 to 14, more preferably 5-, 6- or 7-membered mono- or polycyclic aromatic hydrocarbon radical which comprises at least 1, where appropriate also 2, 3, 4 or 5 heteroatoms, preferably nitrogen, oxygen and/or sulfur, where the heteroatoms are identical or different. The number of nitrogen atoms is preferably 0, 1, 2, or 3, and that of the oxygen and sulfur atoms is independently 0 or 1. The term "heteroaryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the heteroaryl radical. The bonding to the compounds of the general formula (I) can be effected via any possible ring member of the heteroaryl radical. Examples of suitable "heteroaryl" are pyrrolyl, thienyl, furyl, imidazolyl, thiazolyl, isothiazolyl, oxazolyl, oxadiazolyl, isoxazolyl, pyrazolyl, pyridinyl, pyrimidinyl, pyridazinyl, pyrazinyl, indolyl, quinolinyl, isoquinolinyl, imidazolyl, triazolyl, triazinyl, tetrazolyl, phthalazinyl, indazolyl, indolizinyl, quinoxalinyl, quinazolinyl, pteridinyl, carbazolyl, phenazinyl, phenoxazinyl, phenothiazinyl, acridinyl.

For the purposes of the present invention, the terms "alkylcycloalkyl", "cycloalkylalkyl", "alkyl-heterocyclyl", "heterocyclylalkyl", "alkyl-aryl", "arylalkyl", "alkyl-heteroaryl" and "heteroarylalkyl" mean that alkyl, cycloalkyl, heterocycl, aryl and heteroaryl are each as defined above, and the cycloalkyl, heterocyclyl, aryl and heteroaryl radical is bonded to the compounds of the general formula (I) via an alkyl radical, preferably $C_1$-$C_8$-alkyl radical, more preferably $C_1$-$C_4$-alkyl radical.

The term "alkyloxy" or "alkoxy" for the purposes of this invention refers to an alkyl radical according to above definition that is attached to an oxygen atom. The attachment to the compounds of the general formula (I) is via the oxygen atom. Examples are methoxy, ethoxy and n-propyloxy, propoxy, isopropoxy. Preferred is "$C_1$-$C_4$-alkyloxy" having the indicated number of carbon atoms.

The term "eycloalkyloxy" or "cycloalkoxy" for the purposes of this invention refers to a cycloalkyl radical according to above definition that is attached to an oxygen atom. The attachment to the compounds of the general formula (I) is via the oxygen atom. Examples are cyclopropyloxy, cyclobutyloxy, cyclopentyloxy, cyclohexyloxy, cycloheptyloxy, cyclooctyloxy. Preferred is "$C_3$-$C_9$cycloalkyloxy" having the indicated number of carbon atoms.

The term "heterocyclyloxy" for the purposes of this invention refers to a heterocyclyl radical according to above definition that is attached to an oxygen atom. The attachment to the compounds of the general formula (I) is via the oxygen atom. Examples are pyrrolidinyloxy, thiapyrroiidinyloxy, piperidinyloxy, piperazinyloxy.

The term "aryloxy" for the purposes of this invention refers to an aryl radical according to above definition that is attached to an oxygen atom. The attachment to the compounds of the general formula (I) is via the oxygen atom. Examples are phenyloxy, 2-naphthyloxy, 1-naphthyloxy, biphenyloxy, indanyloxy. Preferred is phenyloxy.

The term "heteroaryloxy" for the purposes of this invention refers to a heteroaryl radical according to above definition that is attached to an oxygen atom. The attachment to the compounds of the general formula (I) is via the oxygen atom. Examples are pyrrolyloxy, thienyloxy, furyloxy, imidazolyloxy, thiazolyloxy.

The term "halogen", "halogen atom", "halogen substituent" or "Hal" for the purposes of this invention refers to one or, where appropriate, a plurality of fluorine (F, fluoro), bromine (Br, bromo), chlorine (Cl, chioro), or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. "Halogen" preferably means a fluorine, chlorine or bromine atom. Fluorine is most preferred, when the halogens are substituted on an alkyl (haloalkyl) or alkoxy group (e.g. $CF_3$ and $CF_3O$).

The term "hydroxyl" means an OH group.

The term "composition", as in pharmaceutical composition, for the purposes of this invention is intended to encompass a product comprising the active ingredient(s), and the inert ingredient(s) that make up the carrier, as well as any product which results, directly or indirectly, from combination, complexation. or aggregation of any two or more of the ingredients, or from dissociation of one or more of the ingredients, or from other types of reactions, or interactions of one or more of the ingredients. Accordingly, the pharmaceutical compositions of the present invention encompass any composition made by admixing a compound of the present invention and a pharmaceutically acceptable carrier.

The terms "administration of" and "administering a" compound should be understood to mean providing a compound of the invention or a prodrug of a compound of the invention to the individualist need.

As used herein, the term "effective amount" refers to any amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a d disorder, or side effect, or a decrease in the rate of advancement of a disease or disorder. The term also includes within its scope amounts effective to enhance normal physiological function.

All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers.

Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or nonchiral phases or by recrystallization from an optionally optically active solvent or with use of an optically active acid or base or by derivatization with an optically active reagent such as, for example, an optically active alcohol, and subsequent elimination of the radical.

The compounds of the invention may be present in the form of their double bond isomers as "pure" E or Z isomers, or in the form of mixtures of these double bond, isomers.

Where possible, the compounds of the invention may be in the form of the tautomers, such as keto-enol tautomers.

It is likewise possible for the compounds of the invention to be in the form of any desired prodrugs such as, for example, esters, carbonates, carbamates, ureas, amides or phosphates, in which cases the actually biologically active form is released only through metabolism. Any compound that can be converted in vivo to provide the bioactive agent (i.e. compounds of the invention) is a prodrug within the scope and spirit of the invention.

Various forms of prodrugs are well known in the art and are described for instance in:
(i) Wermuth C G et al., Chapter 31: 671-696, The Practice of Medicinal Chemistry, Academic Press 1996;
(ii) Bundgaard H, Design of Prodrugs, Elsevier 1985; and
(iii) Bundgaard H, Chapter 5: 131-191, A Textbook of Drug Design and Development, Harwood Academic Publishers 1991.

Said references are incorporated herein by reference.

It is further known that chemical substances are converted in the body into metabolites which may where appropriate likewise elicit the desired biological effect - in some circumstances even in more pronounced form:

Any biologically active compound that was converted in vivo by metabolism from any of the compounds of the invention is a metabolite within the scope and spirit of the invention.

The compounds of the invention can, if they have a sufficiently basic group such as, for example, a secondary or tertiary amine, be converted with inorganic and organic acids into salts. The pharmaceutically acceptable salts of the compounds of the invention are preferably formed with hydrochloric acid, hydrobromic acid, iodic acid, sulfuric acid, phosphoric acid, methanesuifonic acid, p-toluenesulfonic acid, carbonic acid, formic acid, acetic acid, sulfoacetic acid, trifluoroacetic acid, oxalic acid, malonic acid, maleic acid, succinic acid, tartaric acid, racemic acid, malic acid, embonic acid, mandelic acid, fumaric acid, lactic acid, citric acid, taurochoiic acid, glutaric acid, stearic acid, glutamic acid or aspartic acid. The salts which are formed are, inter alia, hydrochlorides, chlorided, hydrobromides, bromides, iodides, sulfates, phosphates, methanesulfonates, tosylates, carbonates, bicarbonates, formates, acetates, sulfoacetates, triflates, oxalates, malonates, maleates, succinates, tartrates, malates, embonates, mandelates, fumarates, lactates, citrates, glutarates, stearates, aspartates and glutamates. The stoichiometry of the salts formed from the compounds of the invention may moreover be an integral or non-integral multiple of one.

The compounds of the invention can, if they contain a sufficiently acidic group such as, for example, the carboxy, sulfonic acid, phosphoric acid or a phenolic group, be converted with inorganic and organic bases into their physiologically tolerated salts. Examples of suitable inorganic bases are ammonium, sodium hydroxide, potassium hydroxide, calcium hydroxide, and of organic bases are ethanolamine, diethanolamine, triethanolamine, ethyl-enediamine, t-butylamine, t-octylamine, dehydroabietylamine, cyclohexylamine, dibenzylethylene-diamine and lysine. The stoichiometry of the salts formed from the compounds of the invention can moreover be an integral or non-integral multiple of one.

It is likewise possible for the compounds of the invention to be in the form of their solvates and, in particular, hydrates which can be obtained for example by crystallization from a solvent or from aqueous solution. It is moreover possible for one, two, three or any number of solvate or water molecules to combine with the compounds of the invention to give solvates and hydrates.

By the term "solvate" is meant a hydrate, an alcoholate, or other solvate of crystallization.

It is known that chemical substances form solids which exist in different order states which are referred to as polymorphic forms or modifications. The various modifications of a polymorphic substance may differ greatly in their physical properties. The compounds of the invention can exist in various polymorphic forms and certain, modifications may moreover be metastable. All these polymorphic forms of the compounds are to be regarded as belonging to the invention.

The compounds can be prepared by general method A, B and C shown below. In all preparative methods, all starting material is known or may easily be prepared from known starting materials.

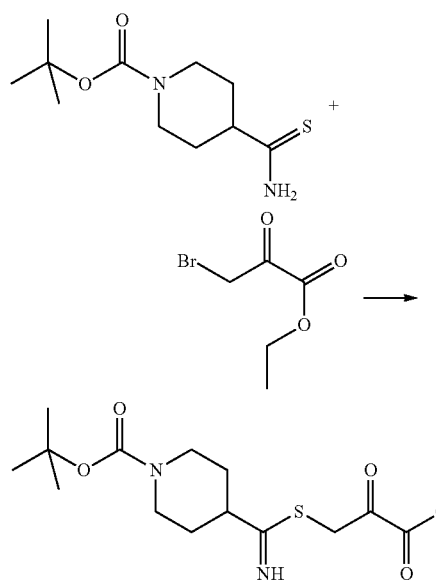

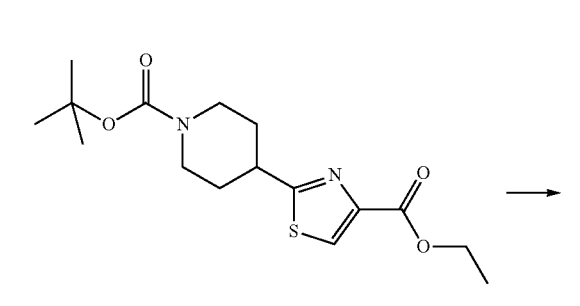

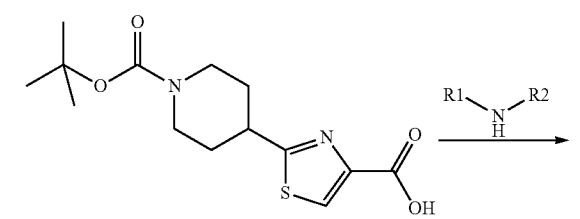

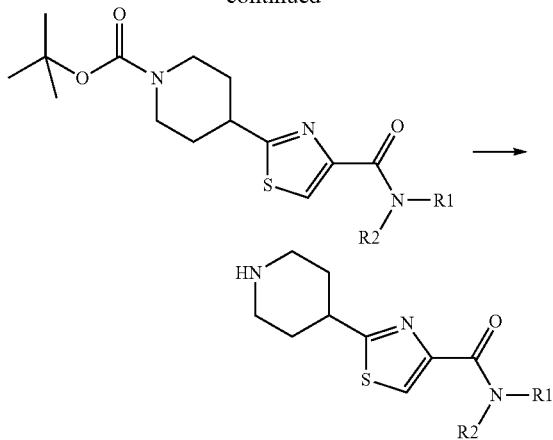

Method A—Coupling of piperazin to 1 eq acyl chloride or carboxyl chloride in a polar solvent at −20° to 50° C., most preferably 0° to 20° C.

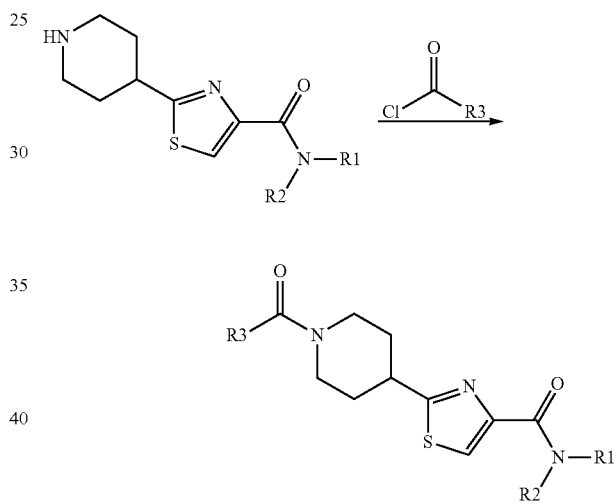

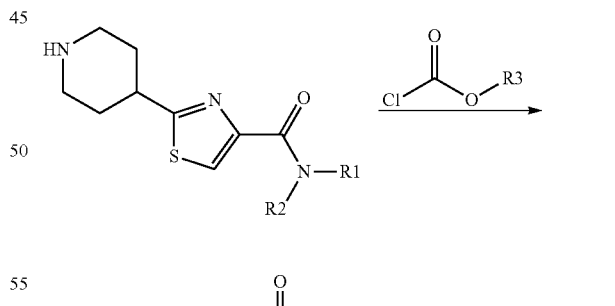

Method B-Coupling of piperazin to 1 eq isocyanate in a polar solvent at −20° to 50° C., most preferably 0° to 20° C.

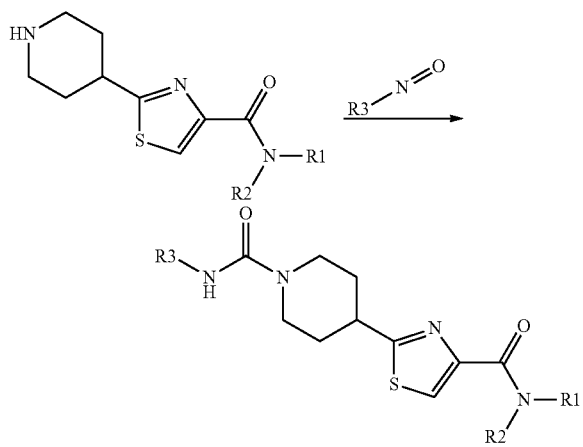

Method C-Coupling of piperazin to 1 eq sulfonyl chloride in a polar solvent at −20° to 50° C., most preferably 0° to 20° C.

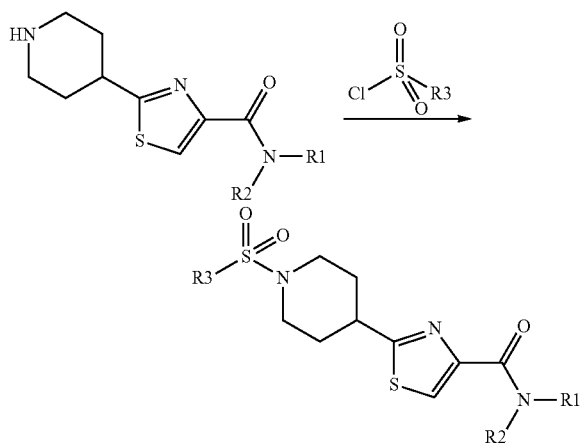

Method D-Coupling of piperazin to 1 eq bromide in a polar solvent at −20° to 50° C., most preferably 0° to 20° C.

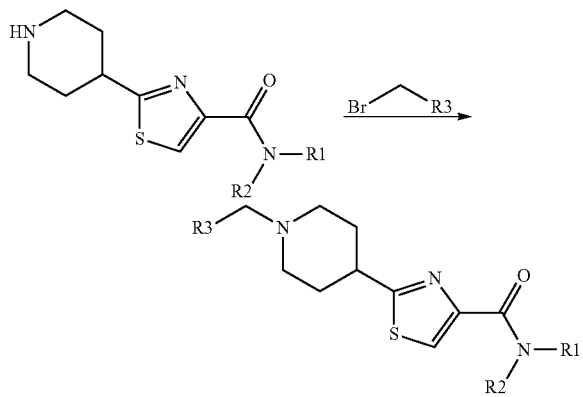

The compounds of the formula (I) and also the starting materials for their preparation are, are prepared by methods as described in the examples or by methods known per se, as described in the literature (for example in standard works, such as Houben-Weyl, Methoden der Organischen Chemie [Methods of Organic Chemistry], Georg Thieme Verlag, Stuttgart; Organic Reactions, John Wiley & Sons, Inc., New York), to be precise under reaction conditions which are known and suitable for the said reactions. Use can also be made here of variants which are known per se, but are not mentioned here in greater detail.

The starting materials for the claimed process may, if desired, also be formed in situ by not isolating them from the reaction mixture, but instead immediately converting them further into the compounds of the formula (I). On the other hand, it is possible to carry out the reaction stepwise.

Preferably, the reaction of the compounds is carried out in the presence of a suitable solvent, which is preferably inert under the respective reaction conditions. Examples of suitable solvents are hydrocarbons, such as hexane, petroleum ether, benzene, toluene or xylene; chlorinated hydrocarbons, such as trichlorethylene, 1,2-dichloroethane, tetrachloromethane, chloroform or di-chloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, dimethylformamide (DMF) or N-methyl pyrrolidinone (NMP); nitriles, such as acetonitrile; sulfoxides, such as dimethyl sulfoxide (DMSO); nitro compounds, such as nitromethane or nitrobenzene; esters, such as ethyl acetate, or mixtures of the said solvents or mixtures with water. Polar solvents are in general preferred. Examples for suitable polar solvents are chlorinated hydrocarbons, alcohols, glycol ethers, nitriles, amides and sulfoxides or mixtures thereof. More preferred are amides, especially di-methylformamide (DMF).

As stated above, the reaction temperature is between about −100° C. and 300° C., depending on the reaction step and the conditions used.

Reaction times are generally in the range between some minutes and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 min and 48 hrs.

A base of the formula (I) can be converted into the associated acid-addition salt using an acid, for example by reaction of equivalent amounts of the base and the acid in a preferably inert solvent, such as ethanol, followed by evaporation. Suitable acids for this reaction are, in particular, those which give physiologically acceptable salts. Thus, it is possible to use inorganic acids, for example sulfuric acid, sulfurous acid, dithionic acid, nitric acid, hydrohalic acids, such as hydrochloric acid or hydrobromic acid, phosphoric acids, such as, for example, orthophosphoric acid, sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, hexanoic acid, octanoic acid, decanoic acid, hexadecanoic acid, octadecanoic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, trimethoxybenzoic acid, adamantanecarboxylic acid, p-toluenesulfonic acid, glycolic acid, embonic acid, chlorophenoxyacetic acid, aspartic acid, glutamic acid, proline, glyoxylic acid, palmitic acid, parachlorophenoxyisobutyric acid, cyclohexane-carboxylic acid, glucose 1-phosphate, naphthalenemono- and -disulfonic acids or laurylsulfuric acid.

Salts with physiologically unacceptable acids, for example picrates, can be used to isolate and/or purify the compounds of the formula (I).

On the other hand, compounds of the formula (I) can be converted into the corresponding metal salts, in particular alkali metal salts or alkaline earth metal salts, or into the corresponding ammonium salts, using bases (for example sodium hydroxide, potassium hydroxide, sodium carbonate or potassium carbonate). Suitable salts are furthermore substituted ammonium salts, for example the dimethyl-, diethyl- and diisopropylammonium salts, monoethanol-, diethanol- and diisopropanolammonium salts, cyclohexyl- and dicyclohexylammonium salts, dibenzylethylenediammonium salts, furthermore, for example, salts with arginine or lysine.

If desired, the free bases of the formula (I) can be liberated from their salts by treatment with strong bases, such as sodium hydroxide, potassium hydroxide, sodium carbonate or potassium carbonate, so long as no further acidic groups are present in the molecule, in the cases where the compounds of the formula (I) have free acid groups, salt formation can likewise be achieved by treatment with bases. Suitable bases are alkali metal hydroxides, alkaline earth metal hydroxides or organic bases in the form of primary, secondary or tertiary amines.

Every reaction step described herein can optionally be followed by one or more working up procedures and/or isolating procedures. Suitable such procedures are known in the art, for example from standard works, such as Houben-Weyl, Methoden der organischen Chemie [Methods of Organic Chemistry], Georg-Thieme-Verlag, Stuttgart). Examples for such procedures include, but are not limited to evaporating a solvent, distilling, crystallization, fractionised crystallization, extraction procedures, washing procedures, digesting procedures, filtration procedures, chromatography, chromatography by HPLC and drying procedures, especially drying procedures in vacuo and/or elevated temperature.

The object of the present invention has surprisingly been solved in another aspect by providing a process of manufacturing a compound of the invention, comprising the steps:

a) 4-thiocarbamoyl-piperidine-1-carboxylic acid tert-butyl ester is reacted with ethyl bromopyruvate to yield 4-(2-ethoxycarbonyl-2-oxo-ethylsulanylcarbonimidoyl)-piperidine-1-carboxylic acid tert-butyl ester ("addition reaction"), and

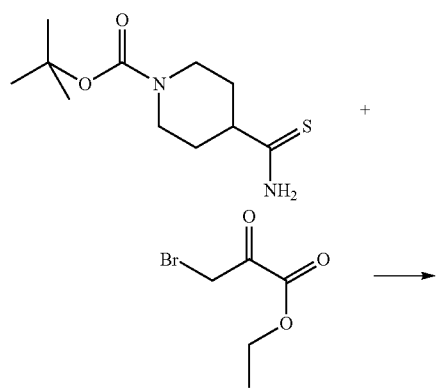

-continued

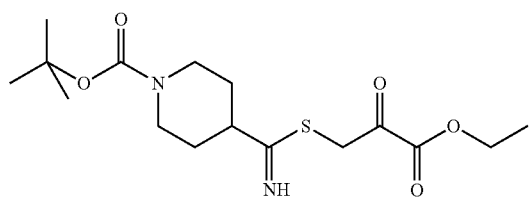

b) 4-(2-ethoxycarbonyl-2-oxo-ethylsulanylcarbonimidoyl)-piperidine-1-carboxylic acid tert-butyl ester is converted into 4-(4-ethoxycarbonyl-thiazol-2-yl)-piperidine-1-carboxylic acid ter-butyl ester ("cyclization"), and

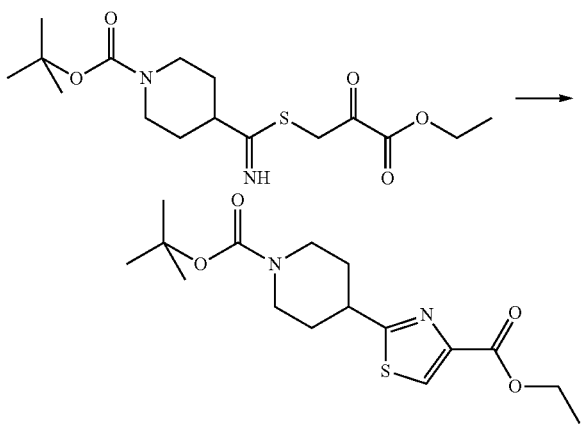

c) 4-(4-ethoxycarbonyl-thiazol-2-yl)-piperidine-1-carboxylic acid ter-butyl ester is reacted with an acid to yield 4-(4-carboxy-thiazol-2-yl)-piperidine-1-carboxylic acid ter-butyl ester ("acidification 1"), and

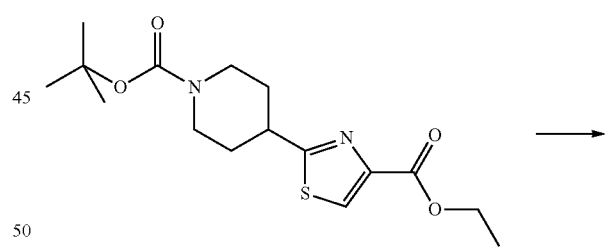

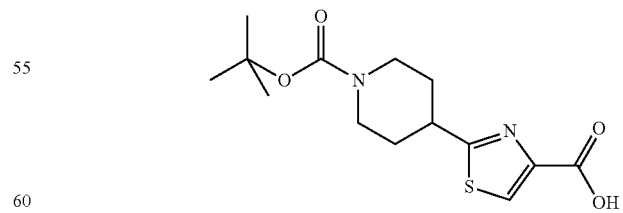

d) 4-(4-carboxy-thiazol-2-yl)-piperidine-1-carboxylic acid ter-butyl ester is reacted with R1-NH—R2, where R1, R2 have the meaning as defined above, to yield 4-{4-(R1R2N-carbonyl)-thiazol-2-yl}-piperidine-1-carboxylic acid ter-butyl ester ("amidation"), and

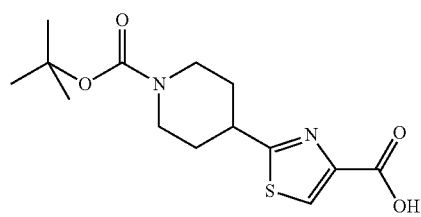

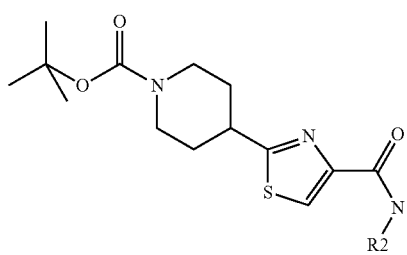

e) 4-{4-(R1R2N-carbonyl)-thiazol-2-yl}-piperidine-1-carboxylic acid ter-butyl ester is reacted with an acid to yield 4-{4-(R1R2N-carbonyl)-thiazol-2-yl}-piperidine ("acidification 2"), and

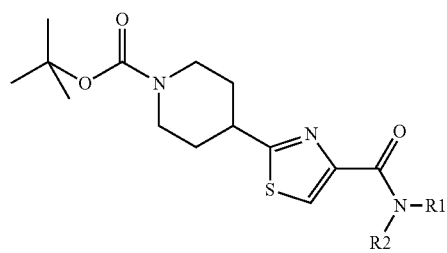

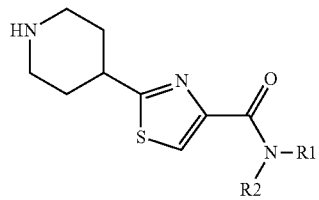

f1) 4-{4-(R1R2N-carbonyl)-thiazol-2-yl}-piperidine is reacted with acyl chloride to yield 4-{4-(R1R2N-carbonyl)-thiazol-2-yl}-piperidine-1-carbonyl-R3 ("acylation"), where R3 has the meaning as defined above, or -continued

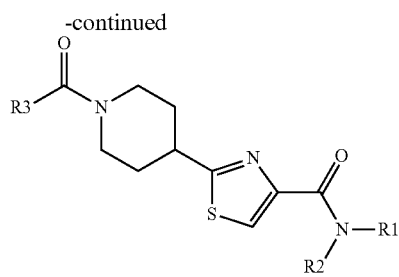

f2) 4-{4-(R1R2N-carbonyl)-thiazol-2-yl}-piperidine is reacted with isocyanate to yield 4-{4-(R1R2N-carbonyl)-thiazol-2-yl}-piperidine-1-carbamoyl-R3 ("carbamoylation"), where R3 has the meaning as defined above, or

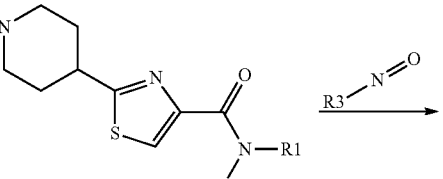

f3) 4-{4-(R1R2N-carbonyl)-thiazol-2-yl}-piperidine is reacted with sulfonyl chloride to yield 4-{4-(R1R2N-carbonyl)-thiazol-2-yl}-piperidine-1-sulfonyl-R3 ("sulfonylation"), where R3 has the meaning as defined above, or

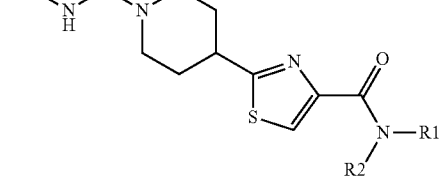

f4) 4-{4-(R1R2N-carbonyl)-thiazol-2-yl}-piperidine is reacted with carboxy-chloride to yield 4-{4-(R1R2N-carbonyl)-thiazol-2-yl}-piperidine-1-carboxyl-R3 ("carboxylation") where R3 has the meaning as defined above, or

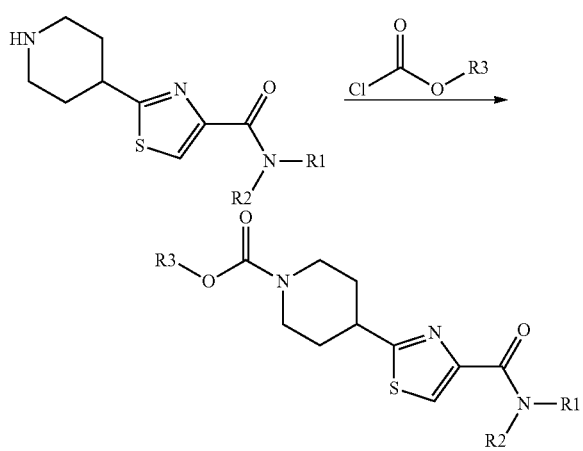

f5) 4-{4-(R1R2N-carbonyl)-thiazol-2-yl}-piperidine is reacted with a bromide to yield 4-{4-(R1R2N-carbonyl)-thiazol-2-yl}-piperidine-1-R3 ("alkylation"), where R3 has the meaning as defined above.

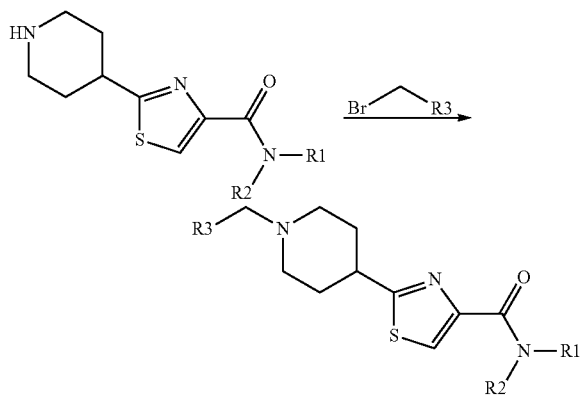

The compounds of the invention are surprisingly characterized by a strong and/or selective inhibition of 11-β-HSD-1 enzyme.

Due to their surprisingly strong and/or selective enzyme inhibition, the compounds of the invention can be advantageously administered at lower doses compared to other less potent or selective inhibitors of the prior art while still achieving equivalent or even superior desired biological effects, in addition, such a dose reduction may advantageously lead to less or even no medicinal adverse effects. Further, the high inhibition selectivity of the compounds of the invention may translate into a decrease of undesired side effects on its own regardless of the dose applied.

The compounds of the invention are selective inhibitors of the 11-β-HSD-1 enzyme. Thus, the present invention relates to the use of the compounds of the present invention for inhibiting the reductase activity of 11-β-hydroxysteroid dehydrogenase-1, which is responsible for the conversion of cortisone to Cortisol.

The compounds of the invention being 11-β-HSD-1 inhibitors generally have an inhibition constant IC50 of less than about 500 nM, and preferably less than about 100 nM. Generally, the IC50 ratio 11-β-HSD-2 to 11-β-HSD-1 of a compound of the invention is at least about two or more, and preferably about ten or greater. Even more preferred are compounds with an IC50 ratio for 11-β-HSD-2 to 11-β-HSD-1 of about 20 or greater. For example, compounds of the present invention ideally demonstrate an inhibition constant IC50 against 11-β-HSD-2 greater than about 1000 nM, and preferably greater than 5000 nM.

The present invention includes the use of an 11-β-HSD-1 inhibitor for the treatment, control, amelioration, prevention, delaying the onset of or reducing the risk of developing physiological and pathophysiological conditions that are described herein, as mediated by excess or uncontrolled amounts of cortisol and/or other corticosteroids in a mammalian patient, particularly a human, by the administration of an effective amount of a compound of the invention or a pharmaceutically acceptable salt or solvate thereof, inhibition of 11-β-HSD-1 enzyme limits the conversion of cortisone, which is normally inert, to Cortisol, which can cause or contribute to the symptoms of the herein described physiological and pathophysiological conditions if present in excessive amounts.

The object of the present invention has surprisingly been solved in another aspect by providing the use of a compound of the invention as 11-β-HSD-1 inhibitor.

The terms "inhibiting, inhibition and/or retardation" are intended to refer for the purposes of the present invention to as follows: "partial or complete inhibiting, inhibition and/or retardation". In this case, it is within the specialist knowledge of the average person skilled in the art to measure and determine such inhibiting, inhibition, and/or retardation by means of the usual methods of measurement and determination. Thus, a partial inhibiting, inhibition and/or retardation, for example, can be measured and determined in relation to a complete inhibiting, inhibition and/or retardation.

The object of the present invention has surprisingly been solved in another aspect by providing a medicament comprising at least one compound of the invention.

The object of the present invention has surprisingly been solved in another aspect by providing a medicament comprising at least one compound of the invention for use in the treatment and/or prophylaxis of physiological and/or pathophysiological conditions, which are caused, mediated and/or propagated by high Cortisol levels. A corresponding use for the preparation of a medicament for the treatment and/or prophylaxis of the aforementioned conditions is intended to be comprised.

The object of the present invention has surprisingly been solved in another aspect by providing a medicament comprising at least one compound of the invention for use in the treatment and/or prophylaxis of physiological and/or pathophysiological conditions selected from the group consisting of metabolic syndrome, diabetes, especially non-insulin dependent diabetes mellitus, prediabetes, insulin resistance, low glucose tolerance, hyperglycemia, obesity and weight-related disorders, lipid disorders such as dyslipidemia, hyperlipidemia, hypertriglyceridemia, hypercholesterolemia, low HDL levels or high LDL levels, glaucoma, osteoporosis, glucocorticoid-mediated effects on neuronal function, such as cognitive impairment, anxiety or depression, neurodegenerative disease, immune disorders such as tuberculosis, leprosy or psoriasis, hypertension, atherosclerosis and its sequelae, vascular restenosis, cardiovascular diseases, pancreatitis, retinopathy, neuropathy and nephropathy. A corresponding use for the preparation of a medicament for the treatment and/or prophylaxis of the aforementioned conditions is intended to be comprised.

In another aspect of the invention, a method of treating a condition selected from the group consisting of: hyperglycemia, low glucose tolerance, insulin resistance, obesity, lipid disorders, dyslipidemia, hyperiipidemia, hypertriglyceridemia, hypercholesterolemia, low MEL levels, high LDL levels, atherosclerosis and its sequelae, vascular restenosis, pancreatitis, abdominal obesity, neurodegenerative disease, retinopathy, nephropathy, neuropathy, Metabolic Syndrome, hypertension and other conditions and disorders where insulin resistance is a component, in a mammalian patient in need of such treatment is disclosed, comprising administering to the patient at least one compound of the invention in an amount that is effective to treat said condition.

In another aspect of the invention, a method of delaying the onset of a condition selected from the group consisting of hyperglycemia, low glucose tolerance, insulin resistance, obesity, lipid disorders, dyslipidemia, hyperlipidemia, hypertriglyceridemia, hypercholesterolemia, low EMIL levels, high LDL levels, atherosclerosis and its sequelae, vascular restenosis, pancreatitis, abdominal obesity, neurodegenerative disease, retinopathy, nephropathy, neuropathy, Metabolic Syndrome, hypertension and other conditions and disorders where insulin resistance is a component in a mammalian patient in need of such treatment is disclosed, comprising administering to the patient at least one compound of the invention in an amount that is effective to delay the onset of said condition.

In another aspect of the invention, a method of reducing the risk of developing a condition selected from the group consisting of hyperglycemia, low glucose tolerance, insulin resistance, obesity, lipid disorders, dyslipidemia, hyperlipidemia, hypertriglyceridemia, hypercholesterolemia, low HDL levels, high LDL levels, atherosclerosis and its sequelae, vascular restenosis, pancreatitis, abdominal obesity, neurodegenerative disease, retinopathy, nephropathy, neuropathy, Metabolic Syndrome, hypertension and other conditions and disorders where insulin resistance is a component in a mammalian patient in need of such treatment is disclosed, comprising administering to the patient at least one compound of then invention in an amount that is effective to reduce the risk of developing said condition.

Compounds of the invention may be used in combination with one or more other active substances (ingredients, drugs) in the treatment, prevention, suppression or amelioration of diseases or conditions for which compounds of the invention or the other substances have utility. Typically the combination of the drugs is safer or more effective than either drug alone, or the combination is safer or more effective than would it be expected based on the additive properties of the individual drugs. Such other drug(s) may be administered, by a route and in an amount commonly used contemporaneously or sequentially with a compound of the invention. When a compound of the invention is used contemporaneously with one or more other drugs, a combination product containing such other drug(s) and the compound of the invention is preferred. However, combination therapy also includes therapies in which the compound of the invention and one or more other drugs are administered on different overlapping schedules. It is contemplated that when used in combination with other active ingredients, the compound of the present invention or the other active ingredient or both may be used effectively in lower doses than when each is used alone. Accordingly, the pharmaceutical compositions of the present invention include those that contain one or more other active ingredients, in addition to a compound of the invention.

Examples of other active substances that may be administered in combination with a compound of the invention, and either administered separately or in the same pharmaceutical composition, include, but are not limited to: dipeptidyl peptidase IV (DP-IV) inhibitors; insulin sensitizing agents including PPARγ agonists such as the glitazones (e.g. troglitazone, ptoglitazone, englitazone, MCC-555, rosiglitazone, and the like) and other PPAR ligands, including PPARα/γ dual agonists, such as KRP-297, and PPARα agonists such as gemfibrozil, clofibrate, fenofibrate and bezafibrate, and biguanides, such as metformin and phenformin; insulin or insulin mimetics; sulfonylureas and other insulin secretagogues such as tolbutamide, glipizide, meglitinide and related materials; α-glucosidase inhibitors, such as acarbose; glucagon receptor antagonists such as those disclosed in WO 98/04528, WO 99/01423, WO 00/39088 and WO 00/69810; GLP-1, GLP-1 analogs, and GLP-1 receptor agonists such as those disclosed in WO 00/42026 and WO 00/59887; GIP, GIP mimetics such as those disclosed in WO 00/58360, and GIP receptor agonists; PACAP, PACAP mimetics, and PACAP receptor 3 agonists such as those disclosed in WO 01/23420; cholesterol lowering agents such as HMG-CoA reductase inhibitors (lovastatin, simvastatin, pravastatin, cerivastatin, fluvastatin, atorvastatin, itavastatin, rosuvastatin, and other stating), bile-acid sequestrants (cholestyramine, colestipol, and dialkylaminoalkyl derivatives of a cross-linked dextran), nicotinyl alcohol, nicotinic acid or a salt thereof, inhibitors of cholesterol absorption, such as ezetimibe and beta-sitosterol, acyl CoA:cholesterol acyltransferase inhibitors, such as, for example, avasimibe, and anti-oxidants, such as probucol; PPARδ agonists, such as those disclosed in WO 97/28149; antiobesity compounds such as fenfluramine, dexfenfluramine, phentermine, sibutramine, orlistat, neuropeptide Y1 or Y5 antagonists, CB 1 receptor inverse agonists and antagonists, adrenergic receptor agonists, melanocortin- receptor agonists, in particular melanocortin-4 receptor agonists, ghrelin antagonists, and melanin-concentrating hormone (MCH) receptor antagonists; ileal bile acid transporter inhibitors; agents intended for use in inflammatory conditions other than glucocorticoids, such as aspirin, non-steroidal anti-inflammatory drugs, azulfidine, and selective cyclooxygenase-2 inhibitors; protein tyrosine phosphatase 1B (PTP-1B) inhibitors; antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, ciiexetil, eprosartan, irbesartan, losartan, tasosartan, telnisartan, and valsartan; and inhibitors of cholesteryl ester transfer protein (CETP). The above combinations include a compound of structural formula I, or a pharmaceutically acceptable salt or solvate thereof, with one or more other active compounds. Non limiting examples include combinations of compounds of structural formula I with two or more active compounds selected from biguanides, sulfonylureas, HMG-CoA reductase inhibitors, PPAR agonists, PTP-1 B inhibitors, DP-IV inhibitors, and anti-obesity compounds.

Antiobesity compounds that can be combined with compounds of the invention include fenfluramine, dexfenfluramine, phentermine, sibutramine, orlistat, neuropeptide Y1 or Y5 antagonists, cannabinoid CB 1 receptor antagonists or inverse agonists, melanocortin receptor agonists, in particular, melanocortin-4 receptor agonists, ghrelin antagonists, and melaninconcentrating hormone (MCH) receptor antagonists. For a review of antiobesity compounds that can be combined with compounds of structural formula I, see S. Chaki et al., "Recent advances in feeding suppressing agents: potential therapeutic strategy for the treatment of obesity," Expert Opin. Ther. Patents, 11: 1677-1692 (2001) and D. Spanswick and K. Lee, "Emerging antiobesity drugs," Expert Opin. Emerging Drugs, 8: 217-237 (2003).

Neuropeptide Y5 antagonists that can be combined with compounds of the invention include those disclosed in U.S.

Pat. No. 6,335,345 and WO 01/14376; and specific compounds identified as GW59884A; GW569180A; LY366377; and COP-71683A.

Cannabinoid CB 1 receptor antagonists that can be combined with compounds of formula I include those disclosed in WO 03/007887; U.S. Pat. No. 5,624,941, such as rimonabant; WO 02/076949, such as SLV-319; U.S. Pat. No. 6,028,084; WO 98/41519; WO 00/10968; WO 99/02499; U.S. Pat. No. 5,532,237; and U.S. Pat. No. 5,292,736.

Melanocortin receptor agonists that can be combined with compounds of the invention include those disclosed in WO 03/009847; WO 02/068388; WO 99/64002; WO 00/74679; WO 01/70708; and WO 01/70337 as well as those disclosed in J. D. Speake et al., "Recent advances in the development of melanocortin-4 receptor agonists, Expert Opin. Ther. Patents, 12: 1631-1638(2002).

In another aspect of the invention, a method of treating a condition selected from the group consisting of hyperglycemia, low glucose tolerance, insulin resistance, obesity, lipid disorders, dyslipidemia, hyperiipidemia, hypertriglyceridemia, hypercholesterolemia, low HDL levels, high LDL levels, atherosclerosis and its sequelae, vascular restenosis, pancreatitis, abdominal obesity, neurodegenerative disease, retinopathy, nephropathy, neuropathy, Metabolic Syndrome, hypertension and other conditions and disorders where insulin resistance is a component, in a mammalian patient in need of such treatment, comprising administering to the patient an effective amount of at least one compound of the invention and at least one compound selected from the group consisting of: dipeptidyl peptidase-IV (DP-IV); inhibitors; insulin sensitizing agents selected from the group consisting of PPARγ agonists, PPARα agonists, PPARα/γ dual agonists, and biguanides; insulin and insulin mimetics; sulfonylureas and other insulin secretagogues; α-glucosidase inhibitors; glucagon receptor antagonists; GLP-1, GLP-1 analogs, and GLP-1 receptor agonists; GIP, GIP mimetics, and GIP receptor agonists; PACAP, PACAP mimetics, and PACAP receptor 3 agonists; cholesterol lowering agents selected from the group consisting of HMG-CoA reductase inhibitors, sequestrants, nicotinyl alcohol, nicotinic acid and salts thereof, inhibitors of cholesterol absorption, acyl CoA:cholesterol acyltransferase inhibitors, and anti-oxidants; PPARδ agonists; anti-obesity compounds; ileal bile acid transporter inhibitors; anti-inflammatory agents, excluding glucocorticoids; protein tyrosine phosphatase 1B (PTP-1 B) inhibitors; and antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, ciiexetil, eprosartan, irbesartan, losartan, tasosartan, telmisartan, and valsartan; said compounds being administered to the patient in an amount that is effective to treat said condition. Dipeptidyl peptidase-IV inhibitors that can be combined with compounds of structural formula I include those disclosed in WO 03/004498, WO 03/004496; EP 1 258 476; WO 02/083128; WO 02/062764; WO 03/00025; WO 03/002530; WO 03/002531; WO 03/002553; WO 03/002593; WO 03/000180; and WO 03/000181. Specific DP-IV inhibitor compounds include isoleucine thiazolidide; NVP-DPP728; P32/98; and LAF 237.

In another aspect of the invention, a method of treating a condition selected from the group consisting of hypercholesterolemia, atherosclerosis, low HDL levels, high LDL levels, hyperlipidemia, hypertriglyceridemia, and dyslipidemia, in a mammalian patient in need of such treatment is disclosed, comprising administering to the patient a therapeutically effective amount of at least one compound of the invention and an HMG-CoA reductase inhibitor.

More particularly, in another aspect of the invention, a method of treating a condition selected from the group consisting of hypercholesterolemia, atherosclerosis, low HDL levels, high LDL levels, hyperiipidemia, hypertriglyceridemia and dyslipidemia, in a mammalian patient in need of such treatment is disclosed, wherein the HMG-CoA reductase inhibitor is a statin.

Even more particularly, in another aspect of the invention, a method of treating a condition selected from the group consisting of hypercholesterolemia, atherosclerosis, low HAL levels, high LDL levels, hyperiipidemia, hypertriglyceridemia and dyslipidemia, in a mammalian patient in need of such treatment is disclosed, wherein the HMG-CoA reductase inhibitor is a statin selected from the group consisting of lovastatin, simvastatin, pravastatin, cerivastatin, fluvastatin, atorvastatin, itavastatin and rosuvastatin.

In another aspect of the invention, a method of reducing the risk of developing a condition selected from the group consisting of hypercholesterolemia, atherosclerosis, low HDL levels, high LDL levels, hyperiipidemia, hypertriglyceridemia and dyslipidemia, and the sequelae of such conditions is disclosed comprising administering to a mammalian patient in need of such treatment a therapeutically effective amount of at least one compound of the invention and an HMG-CoA reductase inhibitor.

In another aspect of the invention, a method for delaying the onset or reducing the risk of; developing atherosclerosis in a human patient in need of such treatment is disclosed comprising administering to said patient an effective amount of at least one compound of the invention and an HMG-CoA reductase inhibitor.

More particularly, a method for delaying the onset or reducing the risk of developing atherosclerosis in a human patient in need of such treatment is disclosed, wherein the HMG-CoA reductase inhibitor is a statin.

Even more particularly, a method for delaying the onset or reducing the risk of developing atherosclerosis in a human patient in need of such treatment is disclosed, wherein the HMG-CoA reductase inhibitor is a statin selected from the group consisting of: lovastatin, simvastatin, pravastatin, cerivastatin, ftuvastatin, atorvastatin, itavastatin, and rosuvastatin.

Even more particularly, a method for delaying the onset or reducing the risk of developing atherosclerosis in a human patient in need of such treatment is disclosed, wherein the statin is simvastatin.

In another aspect of the invention, a method for delaying the onset or reducing the risk of developing atherosclerosis in a human patient in need of such treatment is disclosed, wherein the HMG-CoA reductase inhibitor is a statin and further comprising administering a cholesterol absorption inhibitor.

More particularly, in another aspect of the invention, a method for delaying the onset or reducing the risk of developing atherosclerosis in a human patient in need of such treatment is disclosed, wherein the HMG-CoA reductase inhibitor is a statin and the cholesterol absorption inhibitor is ezetimibe.

In another aspect of the invention, a medicament according to above aspects and embodiments is provided, wherein in such medicament comprises at least one additional pharmacologically active substance (drug, ingredient).

In a preferred embodiment the at least one pharmacologically active substance is a substance as described herein.

In another aspect of the invention, a medicament according to above aspects and embodiments is provided, wherein the medicament is applied before and/or during and/or after treatment with at least one additional pharmacologically active substance.

In a preferred embodiment the at least one pharmacologically active substance is a substance as described herein.

In another aspect of the invention, a pharmaceutical composition comprising a therapeutically effective amount of at least one compound of the invention is provided.

In a preferred embodiment, the pharmaceutical composition contains at least one additional compound selected from the group consisting of physiologically acceptable excipients, auxiliaries, adjuvants, diluents, carriers and/or additional pharmaceutically active substance other than the compounds of the invention.

In another aspect of the invention, a pharmaceutical composition is disclosed which comprises at least one compound of the invention, a compound selected from the group consisting of: DP-IV inhibitors; insulin I sensitizing agents selected from the group consisting of PPARα agonists; PPARγ agonists, PPARα/γ dual agonists, and biguanides; insulin and insulin mimetics; sulfonylureas and other insulin secretagogues; oc-glucosidase inhibitors; glucagon receptor antagonists; GLP-1, GLP-1 analogs, and GLP-1 receptor agonists; GIP, GIP mimetics, and GIP receptor agonists; PACAP, PACAP mimetics, and PACAP receptor 3 agonists; cholesterol lowering agents selected from the group consisting of HMG-CoA reductase inhibitors, sequestrants, (nicotinyl alcohol, nicotinic acid or a salt thereof, inhibitors of cholesterol absorption, acyl CoA:cholesterol acyltransferase inhibitors, and antioxidants; PPARδ agonists; antiobesity compounds; ileal bile acid transporter inhibitors; anti-inflammatory agents other than glucocorticoids; protein tyrosine phosphatase 1B (PTP-1B) inhibitors; and antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, iosartan, tasosartan, telmisartan, and valsartan; inhibitors of cholesteryl ester transfer protein (CETP); and a pharmaceutically acceptable carrier.

A further embodiment of the present invention is a process for the manufacture of said pharmaceutical compositions, characterized in that one or more compounds according to the invention and one or more compounds selected from the group consisting of solid, liquid or semiliquid excipients, auxiliaries, adjuvants, diluents, carriers and pharmaceutically active agents other than the compounds according to the invention, are converted in a suitable dosage form.

In another aspect of the invention, a kit is provided comprising a therapeutically effective amount of at least one compound of the invention and/or at least one pharmaceutical composition as described herein and a therapeutically effective amount of at least one further pharmacologically active substance other than the compounds of the invention.

The pharmaceutical compositions of the present invention may be administered by any means that achieve their intended purpose. For example, administration may be by oral, parenteral, topical, enteral, intravenous, intramuscular, inhalant, nasal, intraarticular, intraspinal, transtracheal, transocular, subcutaneous, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired. Parenteral administration is preferred. Oral administration is especially preferred.

Suitable dosage forms include, but are not limited to capsules, tablets, pellets, dragees, semi-solids, powders, granules, suppositories, ointments, creams, lotions, inhalants, injections, cataplasms, gels, tapes, eye drops, solution, syrups, aerosols, suspension, emulsion, which can be produced according to methods known in the art, for example as described below;

tablets: mixing of active ingredient/s and auxiliaries, compression of said mixture into tablets (direct compression), optionally granulation of part of mixture before compression.

capsules: mixing of active ingredient/s and auxiliaries to obtain allowable powder, optionally granulating powder, filling powders/granulate into opened capsules, capping of capsules.

semi-solids (ointments, gels, creams): dissolving/dispersing active ingredient/s in an aqueous or fatty carrier; subsequent mixing of aqueous/fatty phase with complementary fatty/aqueous phase, homogenization (creams only).

suppositories (rectal and vaginal): dissolving/dispersing active ingredient/s in carrier material liquified by heat (rectal: carrier material normally a wax; vaginal: carrier normally a heated solution of a gelling agent), casting said mixture into suppository forms, annealing and withdrawal suppositories from the forms.

aerosols: dispersing/dissolving active agent/s in a propellant, bottling said mixture into an atomizer.

In general, non-chemical routes for the production of pharmaceutical compositions and/or pharmaceutical preparations comprise processing steps on suitable mechanical means known in the art that transfer one or more compounds of the invention into a dosage form suitable for administration to a patient in need of such a treatment. Usually, the transfer of one or more compounds of the invention into such a dosage form comprises the addition of one or more compounds, selected from the group consisting of carriers, excipients, auxiliaries and pharmaceutical active ingredients other than the compounds of the invention. Suitable processing steps include, but are not limited to combining, milling, mixing, granulating, dissolving, dispersing, homogenizing, casting and/or compressing the respective active and non-active ingredients. Mechanical means for performing said processing steps are known in the art, for example from Ullmann's Encyclopedia of Industrial Chemistry, 5th Edition. In this respect, active ingredients are preferably at least one compound of the invention and one or more additional compounds other than the compounds of the invention, which show valuable pharmaceutical properties, preferably those pharmaceutical active agents other than the compounds of the invention, which are disclosed herein.

Particularly suitable for oral use are tablets, pills, coated tablets, capsules, powders, granules, syrups, juices or drops, suitable for rectal use are suppositories, suitable for parenteral use are solutions, preferably oil-based or aqueous solutions, furthermore suspensions, emulsions or implants, and suitable for topical use are ointments, creams or powders. The compounds of the invention may also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, dyes, flavours and/or a plurality of further active ingredients, for example one or more vitamins.

Suitable excipients are organic or inorganic substances, which are suitable for enteral (for example oral), parenteral or topical administration and do not react with the compounds of the invention, for example water, vegetable oils, benzyl alcohols, alkylene glycols, polyethylene glycols, glycerol triacetate, gelatine, carbohydrates, such as lactose, sucrose, mannitol, sorbitol or starch (maize starch, wheat starch, rice starch, potato starch), cellulose preparations and/or calcium phosphates, for example tricalcium phosphate or calcium hydrogen phosphate, magnesium stearate, talc, gelatine, tragacanth, methyl cellulose, hydroxypropylmethylcellulose, sodium carboxymethylcellulose, polyvinyl pyrrolidone and/or vaseline.

If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries include, without limitation, flow-regulating agents and lubricants, for example, silica, talc, stearic acid or salts thereof, such as magnesium stearate or calcium stearate, and/or polyethylene glycol. Dragee cores are provided with suitable coatings, which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices or to provide a dosage form affording the advantage of prolonged action, the tablet, dragee or pill can comprise an inner dosage and an outer dosage component me latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, acetyl alcohol, solutions of suitable cellulose preparations such as acetyl-cellulose phthalate, cellulose acetate or hydroxypropylmethyl-cellulose phthalate, are used. Dye stuffs or pigments may be added to the tablets or dragee coatings, for example, for identification or in order to characterize combinations of active compound doses.

Suitable carrier substances are organic or inorganic substances which are suitable for enteral (e.g. oral) or parenteral administration or topical application and do not react with the novel compounds, for example water, vegetable oils, benzyl alcohols, polyethylene glycols, gelatin, carbohydrates such as lactose or starch, magnesium stearate, talc and petroleum jelly, in particular, tablets, coated tablets, capsules, syrups, suspensions, drops or suppositories are used for enteral administration, solutions, preferably oily or aqueous solutions, furthermore suspensions, emulsions or implants, are used for parenteral administration, and ointments, creams or powders are used for topical application. The compounds of the invention can also be lyophilized and the lyophilizates obtained can be used, for example, for the production of injection preparations.

The preparations indicated can be sterilized and/or can contain excipients such as lubricants, preservatives, stabilizers and/or wetting agents, emuisifiers, salts for affecting the osmotic pressure, buffer substances, colorants, flavourings and/or aromatizers. They can, if desired, also contain one or more further active compounds, e.g. one or more vitamins.

Other pharmaceutical preparations, which can be used orally include push-fit capsules made of gelatine, as well as soft, sealed capsules made of gelatine and a plasticizer such as glycerol or sorbitol. The push-fit capsules can contain the active compounds in the form of granules, which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

The liquid forms in which the novel compositions of the present invention may be incorporated for administration orally include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatine.

Suitable formulations for parenteral administration include aqueous solutions of the active compounds in water-soluble form, for example, water-soluble salts and alkaline solutions/In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400).

Aqueous injection suspensions may contain substances, which increase the viscosity of the suspension, including, for example, sodium carboxymethyl cellulose, sorbitol, and/or dextran, optionally, the suspension may also contain stabilizers.

For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronized form, in which case one or more additional physiologically acceptable solvents may be present, for example ethanol. Inhalation solutions can be administered with the aid of conventional inhalers.

Possible pharmaceutical preparations, which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatine rectal capsules, which consist of a combination of the active compounds with a base. Possible base materials include, for example, liquid triglycerides, polyethylene glycols, or paraffin hydrocarbons.

For use in medicine, the compounds of the present invention will be in the form of pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzdic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic bases, e.g. quaternary ammonium salts.

The pharmaceutical preparations can be employed as medicaments in human and veterinary medicine. As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. Said therapeutic effective amount of one or more of the compounds of the invention is known to the skilled artisan or can be easily determined by standard methods known in the art.

The compounds of the invention and the additional active substances are generally administered analogously to commercial preparations. Usually, suitable doses that are therapeutically effective lie in the range between 0.0005 mg and 1000 mg, preferably between 0.005 mg and 500 mg and especially between 0.5 mg and 100 mg per dose unit. The daily dose is preferably between about 0.001 mg/kg and 10 mg/kg of body weight.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For the purpose of the present invention, all mammalian species are regarded as being comprised. In a preferred embodiment, such mammals are selected from the group consisting of "primate, human, rodent, equine, bovine, canine, feline, domestic animals, cattle, livestock, pets, cow, sheep, pig, goat, horse, pony, donkey, hinny, mule, hare, rabbit, cat, dog, guinea pig, hamster, rat, mouse". More preferably, such mammals are humans. Animal models are of interest for experimental investigations, providing a model for treatment of human diseases.

The specific dose for the individual patient depends, however, on the multitude of factors, for example on the efficacy of the specific compounds employed, on the age, body weight, general state of health, the sex, the kind of diet, on the time and route of administration, on the excretion rate, the kind of administration and the dosage form to be administered, the pharmaceutical combination and severity of the particular disorder to which the therapy relates. The specific therapeutic effective dose for the individual patient can readily be determined by routine experimentation, for example by the doctor or physician, which advises or attends the therapeutic treatment.

In the case of many disorders, the susceptibility of a particular cell to treatment with the subject compounds may be determined by in vitro testing. Typically a culture of the cell is combined with a subject compound at varying concentrations for a period of time sufficient to allow the active agents to show a relevant reaction, usually between about one hour and one week. For in vitro testing, cultured cells from a biopsy sample may be used.

Even without further details, it is assumed that a person skilled in the art will be able to utilise the above description in the broadest scope. The preferred embodiments should therefore merely be regarded as descriptive disclosure, which is absolutely not limiting in any way.

Above and below, all temperatures are indicated in ° C. in the following examples, "conventional work-up" means that, if necessary, the solvent is removed, water is added if necessary, the pH is adjusted, if necessary, to between 2 and 10, depending on the constitution of the end product, the mixture is extracted with ethyl acetate or dichloromethane, the phases are separated, the organic phase is washed with saturated $NaHCO_3$ solution, if desired with water and saturated NaCl solution, is dried over sodium sulfate, filtered and evaporated, and the product is purified by chromatography on silica gel, by preparative HPLC and/or by crystallisation. The purified compounds are, if desired, freeze-dried.

Mass spectrometry (MS): ESI (electrospray ionisation) $(M+H)^+$

LIST OF ABBREVIATIONS AND ACRONYMS

AcOH acetic acid, anh anhydrous, atm atmosphere(s), BOC tert-butoxycarbonyl CDI 1,1'-carbonyl diimidazole, conc concentrated, d day(s), dec decomposition, DMAC NN-dimethylacetamide, DMPU 1,3-dimethyl-3,4,5,6-tetrahydro-2(IH)-pyrimidinone, DMF NN-dimethylformamide, DMSO dimethylsulfoxide, DPPA diphenylphosphoryl azide, EDCI 1-(3-dimethylaminopropyl)-3-ethylcarbodiimide, EtOAc ethyl acetate, EtOH ethanol (100%), $Et_2O$ diethyl ether, $Et_3N$ triethylamine, h hour(s), MeOH methanol, pet. ether petroleum ether (boiling range 30-60° C.), temp, temperature, THF tetrahydrofuran, TFA trifluoroAcOH, Tf trifluoromethanesulfonyl.

The contents of all cited references are hereby incorporated by reference in their entirety. The invention is explained in more detail by means of the following examples without, however, being restricted thereto.

EXAMPLES

Example 1

General Method

To 5.5 g (15.4 mmol) of 4-Thiocarbamoyl-piperidine-1-carboxylic acid tert-butyl ester in 50 ml of ethyl acetate was added 3.4 g (40.9 mmol, 2eq) of sodium acetate and 3.7 ml (26.6 mmol, 1.3 eq) of ethyl bromopyruvate at 5° C. The reaction was allowed to pursue for 16 hrs. After addition of water, the compound was extracted 3X $CH_2Cl_2$. The organic layers were washed with water, dried over $Na_2SO_4$ and concentrated in vacuo. The compound was recristallized in diisopropyl oxyde to give 5.53 g (15.43 mmol, 75%) of a white solid.

To 54.2 g (0.15 mol) of the above compound was added 300 ml of acetic acid and the reaction was heated to 100° C. for 1 h30. The mixture was concentrated, $CH_2Cl_2$ was the added and the organic layer washed with a solution of $NaHCO_3$, dried over $Na_2SO_4$ and concentrated in vacuo to give 45.7 g (0.13 mol, 89%) of the desired cyclized compound which was saponified by addition of Ethanol (300 ml) and 16.1 ml (1.16 mol, 1.2 eq) of a sodium hydroxyde solution (10N) for 16 h at room temperature. After concentration in vacuo and addition of water (300 ml), washing with $CH_2Cl_2$, the solution was then acidified with AcOH. The compound which precipitates is filtered and washed with water to give 34.63 g (0.11 mol, 83%) of a white solid.

To 1.960 g (6.2 mmol) of the free carboxylic acid under $N_2$ was added 20 ml DMF, and 0.974 g (6.2 mmol, 1 eq) of decahydroquinolin-4ol, 2.838 ml (21.9 mmol, 3.5 eq) of diisopropylamine and 2.4 g (6.2 mmol, 1 eq) of HBTU. The mixture was stirred at room temperature for 16 hrs and the reaction quenched with water (100 ml) and the compound extracted with AcOEt (3×) and washed with a solution of NaHCO$_3$, citrique acid 15%, water, NaCl saturated solution, and finally dried over Na$_2$SO$_4$ and concentrated to give 2.42 g (5.3 mmol, 86%) of an oil.

To 2.35 g (5.2 mmol) of the starting material in 20 ml CH$_2$Cl$_2$ was added at 5° C. was added 13 mi of a HCl/dioxanne solution (4M/L). The reaction was allowed to warm up at room temperature and stirred for 16 hrs. After concentration in vacuo, water was added, the compound washed with CH$_2$Cl$_2$, NaOH solution (10 N) was then added, and the compound was finally extracted with CH$_2$Cl$_2$, washed with a saturated solution of NaCl, dried over Na$_2$SO$_4$ and concentrated to give an oil (1.30 g, 3.7 mmol, 7%).

The following compounds were made in a similar way as described above (table 1).

TABLE 1

| Example | Name | LC/MS |
|---|---|---|
| 1.1 | 2-Piperidin-4-yl-thiazole-4-carboxylic acid cyclohexyl-cyclopropyl-amide | Retention time (Rt) = 1.3 M + 1 = 334.1 |
| 1.2 | (Octahydro-quinolin-1-yl)-(2-piperidin-4-yl-thiazol-4-yl)-methanone | Rt = 1.33 M + 1 = 334.1 |

Example 2

Method A

To 200 mg (0.5 mmol) of (Octahydro-quinolin-1-yl)-(2-piperidin-4-yl-thiazol-4-yl)-methanone in 2 ml acetonitrile was added 94.9 mg (0.6 mmol, 1.2 eq) of potassium carbonate and 62.6 µl (0.5 mmol, 1 eq) of 4-fluoro-benzoyl chloride. The mixture was stirred at room temperature for 20 hrs and the reaction quenched with the addition of water. The compound was ex-tracted with AcOEt and then purified by flash chromatography to obtain 79 mg (0.1 mmol, 29%) of an oil.

The following compounds were made in a similar way as described above (table 2).

TABLE 2

| Example | Name | MS |
|---|---|---|
| 2.1 | 3,3-Dimethyl-1-{4-[4-(octahydro-quinoline-1-carbonyl)-thiazol-2-yl]-piperidin-1-yl}-butan-1-one | Rt = 2.62 M + 1 = 432.2 |
| 2.2 | (Octahydro-quinolin-1-yl)-{2-[1-(pyridine-3-carbonyl)-piperidin-4-yl]-thiazol-4-yl}-methanone | M + 1 = 439.2 |
| 2.3 | 2-(1-Cyclohexanecarbonyl-piperidin-4-yl)-thiazole-4-carboxylic acid cyclohexyl-cyclopropyl-amide | M + 1 = 440 |
| 2.4 | 2-(1-Cyclopentanecarbonyl-piperidin-4-yl)-thiazole-4-carboxylic acid cyclohexyl-cyclopropyl-amide | M + 1 = 430.2 |
| 2.5 | 2-(1-Cyclobutanecarbonyl-piperidin-4-yl)-thiazole-4-carboxylic acid cyclohexyl-cyclopropyl-amide | M + 1 = 416 7.82 (s, 2H) 4.40 (m, 1H) 3.75 (m, 2H) 3.32 (m, 5H) 3.07 (m, 2H) 2.67 (m, 2H) 2.05 (m, 6H) 1.73 (m, 6H) 1.57 (m, 2H) 1.23 (m, 2H) 0.53 (m, 2H) 0.37 (m, 2H) |
| 2.6 | 2-(1-Cyclopropanecarbonyl-piperidin-4-yl)-thiazole-4-carboxylic acid cyclohexyl-cyclopropyl-amide | M + 1 = 402.2 |
| 2.7 | 2-[1-(3-Cyclopentyl-propionyl)-piperidin-4-yl]-thiazole-4-carboxylic acid cyclohexyl-cyclopropyl-amide | M + 1 = 458 |
| 2.8 | 2-[1-(2-Ethyl-butyryl)-piperidin-4-yl]-thiazole-4-carboxylic acid cyclohexyl-cyclopropyl-amide | M + 1 = 432.2 |
| 2.9 | 2-[1-(3,3-Dimethyl-butyryl)-piperidin-4-yl]-thiazole-4-carboxylic acid cyclohexyl-cyclopropyl-amide | M + 1 = 432.2 |
| 2.10 | 2-[1-(3-Methyl-butyryl)-piperidin-4-yl]-thiazole-4-carboxylic acid cyclohexyl-cyclopropyl-amide | M + 1 = 418 |
| 2.11 | 2-(1-Isobutyryl-piperidin-4-yl)-thiazole-4-carboxylic acid cyclohexyl-cyclopropyl-amide | M + 1 = 404 |
| 2.12 | 2-(1-Pentanoyl-piperidin-4-yl)-thiazole-4-carboxylic acid cyclohexyl-cyclopropyl-amide | M + 1 = 418 |
| 2.13 | 2-(1-Propionyl-piperidin-4-yl)-thiazole-4-carboxylic acid cyclohexyl-cyclopropyl-amide | M + 1 = 390 |
| 2.14 | 2-(1-Acetyl-piperidin-4-yl)-thiazole-4-carboxylic acid cyclohexyl-cyclopropyl-amide | M + 1 = 376 |
| 2.15 | 2-[1-(Pyridine-3-carbonyl)-piperidin-4-yl]-thiazole-4-carboxylic acid cyclohexyl-cyclopropyl-amide | M + 1 + 439 |
| 2.16 | 2-[1-(4-Trifluoromethoxy-benzoyl)-piperidin-4-yl]-thiazole-4-carboxylic acid cyclohexyl-cyclopropyl-amide | M + 1 = 522 |
| 2.17 | [2-(1-Cyclohexanecarbonyl-piperidin-4-yl)-thiazol-4-yl]-(octahydro-quinolin-1-yl)-methanone | M + 1 = 444.2 |
| 2.18 | [2-(1-Cyclopentanecarbonyl-piperidin-4-yl)-thiazol-4-yl]-(octahydro-quinolin-1-yl)-methanone | M + 1 = 430.2 |
| 2.19 | [2-(1-Cyclobutanecarbonyl-piperidin-4-yl)-thiazol-4-yl]-(octahydro-quinolin-1-yl)-methanone | M + 1 = 416 |
| 2.20 | [2-(1-Cyclopropanecarbonyl-piperidin-4-yl)-thiazol-4-yl]-(octahydro-quinolin-1-yl)-methanone | M + 1 + 402 |
| 2.21 | 3-Cyclopentyl-1-{4-[4-(octahydro-quinoline-1-carbonyl)-thiazol-2-yl]-piperielin-1-yl}-propan-1-one | M + 1 = 458 |

TABLE 2-continued

| Example | Name | MS |
|---|---|---|
| 2.22 | 2-Ethyl-1-{4-[4-(octahydro-quinoline-1-carbonyl)-thiazol-2-yl]-piperidin-1-yl}-butan-1-one | M + 1 = 432.2 |
| 2.23 | 3-Methyl-1-{4-[4-(octahydro-quinoline-1-carbonyl)-thiazol-2-yl]-piperidin-1-yl}-butan-1-one | M + 1 = 418 |
| 2.24 | 2-Methyl-1-{4-[4-(octahydro-quinoline-1-carbonyl)-thiazol-2-yl]-piperidin-1-yl}-propan-1-one | M + 1 = 404 |
| 2.25 | 1-{4-[4-(Octahydro-quinoline-1-carbonyl)-thiazol-2-yl]-piperidin-1-yl}-pentan-1-one | M + 1 = 418 |
| 2.26 | 1-{4-[4-(Octahydro-quinoline-1-carbonyl)-thiazol-2-yl]-piperidin-1-yl}-propan-1-one | M + 1 = 390 |
| 2.27 | 1-{4-[4-(Octahydro-quinoline-1-carbonyl)-thiazol-2-yl]-piperidin-1-yl}-ethanone | M + 1 = 376 |
| 2.28 | (Octahydro-quinolin-1-yl)-{2-[1-(4-trifluoromethoxy-benzoyl)-piperidin-4-yl]-thiazol-4-yl}-methanone | M + 1 = 522 |
| 2.29 | {2-[1-(4-Fluoro-benzoyl)-piperidin-4-yl]-thiazol-4-yl}-(octahydro-quinolin-1-yl)-methanone | M + 1 = 456.2 |
| 2.30 | {2-[1-(4-Fluoro-benzoyl)-piperidin-4-yl]-thiazol-4-yl}-(4-hydroxy-octahydro-quinolin-1-yl)-methanone | M + 1 = 472.1 |
| 2.31 | 1-{4-[4-(4-Hydroxy-octahydro-quinoline-1-carbonyl)-thiazol-2-yl]-piperidin-1-yl}-2-(4-methoxy-phenyl)-ethanone | M + 1 = 498 |
| 2.32 | 4-[4-(4-Hydroxy-octahydro-quinoline-1-carbonyl)-thiazol-2-yl]-piperidine-1-carboxylic acid tert-butyl ester | M + 1 = 450.2 |
| 2.33 | 2-[1-(2-Phenyl-butyryl)-piperidin-4-yl]-thiazole-4-carboxylic acid cyclohexyl-cyclopropyl-amide | M + 1 = 480.2 |
| 2.34 | 2-{1-[2-(4-Methoxy-phenyl)-acetyl]-piperidin-4-yl}-thiazole-4-carboxylic acid cyclohexyl-cyclopropyl-amide | M + 1 = 482.1 |
| 2.35 | 2-[1-(2-Phenoxy-acetyl)-piperidin-4-yl]-thiazole-4-carboxylic acid cyclohexyl-cyclopropyl-amide | M + 1 = 468 |
| 2.36 | 4-[4-(Cyclohexyl-cyclopropyl-carbamoyl)-thiazol-2-yl]-piperidine-1-carboxylic acid tert-butyl ester | M + 1 = 434.1 |
| 2.37 | 1-{4-[4-(Octahydro-quinoline-1-carbonyl)-thiazol-2-yl]-piperidin-1-yl}-2-phenyl-butan-1-one | M + 1 = 480 |
| 2.38 | 2-(4-Methoxy-phenyl)-1-{4-[4-(octahydro-quinoline-1-carbonyl)-thiazol-2-yl]-piperidin-1-yl}-ethanone | M + 1 = 483 |
| 2.37 | 1-{4-[4-(Octahydro-quinoline-1-carbonyl)-thiazol-2-yl]-piperidin-1-yl}-2-phenoxy-ethanone | M + 1 = 468 |
| 2.38 | 4-[4-(Octahydro-quinoline-1-carbonyl)-thiazol-2-yl]-piperidine-1-carboxylic acid tert-butyl ester | |
| 2.39 | 2-Phenyl-1-{4-[4-(piperidine-1-carbonyl)-thiazol-2-yl]-piperidin-1-yl}-butan-1-one | M + 1 = 426 |
| 2.40 | 2-(4-Methoxy-phenyl)-1-{4-[4-(piperidine-1-carbonyl)-thiazol-2-yl]-piperidin-1-yl}-ethanone | M + 1 = 428 |
| 2.41 | 2-Phenoxy-1-{4-[4-(piperidine-1-carbonyl)-thiazol-2-yl]-piperidin-1-yl}-ethanone | M + 1 = 414 |
| 2.42 | 4-[4-(Piperidine-1-carbonyl)-thiazol-2-yl]-piperidine-1-carboxylic acid tert-butyl ester | M + 1 = 380.3 |
| 2.43 | 2-[1-(2-Phenyl-butyryl)-piperidin-4-yl]-thiazole-4-carboxylic acid cyclohexyl-methyl-amide | M + 1 = 454.1 |
| 2.44 | 2-{1-[2-(4-Methoxy-phenyl)-acetyl]-piperidin-4-yl}-thiazole-4-carboxylic acid cyclohexyl-methyl-amide | M + 1 = 456 |
| 2.45 | 2-[1-(2-Phenoxy-acetyl)-piperidin-4-yl]-thiazole-4-carboxylic acid cyclohexyl-methyl-amide | M + 1 = 442.1 |

Example 3

Method B

To 200 mg (0.5 mmol) of (Octahydro-quinolin-1-yl)-(2-piperidin-4-yl-thiazol-4-yl)-methanone in 2 ml DMF was added 101.1 µl (0.5 mmol, 1 eq) of 1-Butyl-4-isocyanato-benzene. The mixture was stirred at 55° C. for 16 hrs and the reaction quenched with the addition of water. The compound was extracted with AcOEt and then purified by flash chromatography to obtain 38 mg (0.07 mmol, 13%) of an oil.

The following compounds were made in a similar way as described above (table 3).

TABLE 3

| Example | Name | MS |
|---|---|---|
| 3.1 | 4-[4-(Octahydro-quinoline-1-carbonyl)-thiazol-2-yl]-piperidine-1-carboxylic acid sec-butylamide | M + 1 = 433 |
| 3.2 | 4-[4-(Octahydro-quinoline-1-carbonyl)-thiazol-2-yl]-piperidine-1-carboxylic acid tert-butylamide | M + 1 = 433<br>7.92 (m, 1H) 5.83 (s, 1H)<br>4.02 (m, 2H) 3.84 (m, 1H)<br>3.21 (m, 2H) 2.78 (m, 4H)<br>2.02-1.32 (m, 16H)<br>1.27 (s, 9H) |
| 3.3 | 4-[4-(Octahydro-quinoline-1-carbonyl)-thiazol-2-yl]-piperidine-1-carboxylic acid propylamide | M + 1 = 419 |
| 3.4 | 4-[4-(Octahydro-quinoline-1-carbonyl)-thiazol-2-yl]-piperidine-1-carboxylic acid ethylamide | M + 1 = 405 |

TABLE 3-continued

| Example | Name | MS |
|---|---|---|
| 3.5 | 4-[4-(Octahydro-quinoline-1-carbonyl)-thiazol-2-yl]-piperidine-1-carboxylic acid cyclopentylamide | M + 1 = 445 |
| 3.6 | 4-[4-(Octahydro-quinoline-1-carbonyl)-thiazol-2-yl]-piperidine-1-carboxylic acid isopropylamide | M + 1 = 419 |
| 3.7 | 4-[4-(Octahydro-quinoline-1-carbonyl)-thiazol-2-yl]-piperidine-1-carboxylic acid pentylamide | M + 1 = 447 |
| 3.8 | 4-[4-(Cyclohexyl-cyclopropyl-carbamoyl)-thiazol-2-yl]-piperidine-1-carboxylic acid sec-butylamide | M + 1 = 433 |
| 3.9 | 4-[4-(Cyclohexyl-cyclopropyl-carbamoyl)-thiazol-2-yl]-piperidine-1-carboxylic acid tert-butylamide | M + 1 = 433 |
| 3.10 | 4-[4-(Cyclohexyl-cyclopropyl-carbamoyl)-thiazol-2-yl]-piperidine-1-carboxylic acid propylamide | M + 1 = 419 |
| 3.11 | 4-[4-(Cyclohexyl-cyclopropyl-carbamoyl)-thiazol-2-yl]-piperidine-1-carboxylic acid ethylamide | M + 1 = 405 |
| 3.12 | 4-[4-(Cyclohexyl-cyclopropyl-carbamoyl)-thiazol-2-yl]-piperidine-1-carboxylic acid cyclopentylamide | M + 1 = 445 |
| 3.13 | 4-[4-(Cyclohexyl-cyclopropyl-carbamoyl)-thiazol-2-yl]-piperidine-1-carboxylic acid isopropylamide | M + 1 = 419 |
| 3.14 | 4-[4-(Cyclohexyl-cyclopropyl-carbamoyl)-thiazol-2-yl]-piperidine-1-carboxylic acid pentylamide | M + 1 = 447 |
| 3.15 | 4-[4-(4-Hydroxy-octahydro-quinoline-1-carbonyl)-thiazol-2-yl]-piperidine-1-carboxylic acid 4-methoxy-benzylamide | M + 1 = 513.2 |
| 3.16 | 4-[4-(4-Hydroxy-octahydro-quinoline-1-carbonyl)-thiazol-2-yl]-piperidine-1-carboxylic acid (4-butyl-phenyl)-amide | M + 1 = 525.2 |
| 3.17 | 3-({4-[4-(Cyclohexyl-cyclopropyl-carbamoyl)-thiazol-2-yl]-piperidine-1-carbonyl}-amino)-propionic acid | M + 1 = 449.1 |
| 3.18 | 4-[4-(Cyclohexyl-cyclopropyl-carbamoyl)-thiazol-2-yl]-piperidine-1-carboxylic acid (4-butyl-phenyl)-amide | M + 1 = 509 |
| 3.19 | 4-[4-(Cyclohexyl-cyclopropyl-carbamoyl)-thiazol-2-yl]-piperidine-1-carboxylic acid 4-methoxy-benzylamide | M + 1 = 497.1 |
| 3.20 | 3-({4-[4-(Octahydro-quinoline-1-carbonyl)-thiazol-2-yl]-piperidine-1-carbonyl}-amino)-propionic acid | M + 1 = 449.1 |
| 3.21 | 4-[4-(Octahydro-quinoline-1-carbonyl)-thiazol-2-yl]-piperidine-1-carboxylic acid (4-butyl-phenyl)-amide | M + 1 = 509 |
| 3.22 | 4-[4-(Octahydro-quinoline-1-carbonyl)-thiazol-2-yl]-piperidine-1-carboxylic acid 4-methoxy-benzylamide | M + 1 = 497.1 |
| 3.23 | 3-({4-[4-(Piperidine-1-carbonyl)-thiazol-2-yl]-piperidine-1-carbonyl}-amino)-propionic acid | M + 1 = 395 |
| 3.24 | 4-[4-(Piperidine-1-carbonyl)-thiazol-2-yl]-piperidine-1-carboxylic acid (4-butyl-phenyl)-amide | M + 1 = 455.1 |
| 3.25 | 4-[4-(Piperidine-1-carbonyl)-thiazol-2-yl]-piperidine-1-carboxylic acid 4-methoxy-benzylamide | M + 1 = 443 |
| 3.26 | 3-({4-[4-(Cyclohexyl-methyl-carbamoyl)-thiazol-2-yl]-piperidine-1-carbonyl}-amino)-propionic acid | M + 1 = 423 |
| 3.27 | 4-[4-(Cyclohexyl-methyl-carbamoyl)-thiazol-2-yl]-piperidine-1-carboxylic acid (4-butyl-phenyl)-amide | M + 1 = 483 |
| 3.28 | 4-[4-(Cyclohexyl-methyl-carbamoyl)-thiazol-2-yl]-piperidine-1-carboxylic acid 4-methoxy-benzylamide | M + 1 = 471.1 |

Example 4

Method C

To 200 mg (0.5 mmol) of (Octahydro-quinolin-1-yl)-(2-piperidin-4-yl-thiazol-4-yl)-methanone in 2 ml acetonitrile was added 94.9 mg (0.6 mmol, 1.2 eq) of potassium carbonate and 44.3 µl (0.5 mmol, 1 eq) of methanesulfonyl chloride. The mixture was stirred at room temperature for 20 hrs and the reaction quenched with the addition of water. The compound was extracted with AcOEt and then purified by flash chromatography to obtain 69 mg (0.1 mmol, 28%) of an oil.

The following compounds were made in a similar way as described above (table 4).

TABLE 4

| Example | Name | MS |
|---|---|---|
| 4.1 | (Octahydro-quinolin-1-yl)-[2-(1-trifluoromethanesulfonyl-piperidin-4-yl)-thiazol-4-yl]-methanone | M + 1 = 466 |
| 4.2 | {2-[1-(Butane-1-sulfonyl)-piperidin-4-yl]-thiazol-4-yl}-(octahydro-quinolin-1-yl)-methanone | M + 1 = 454.1 |
| 4.3 | (Octahydro-quinolin-1-yl)-{2-[1-(propane-1-sulfonyl)-piperidin-4-yl]-thiazol-4-yl}-methanone | M + 1 = 440 |
| 4.4 | [2-(1-Ethanesulfonyl-piperidin-4-yl)-thiazol-4-yl]-(octahydro-quinolin-1-yl)-methanone | M + 1 = 426 |
| 4.5 | 2-(1-Trifluoromethanesulfonyl-piperidin-4-yl)-thiazole-4-carboxylic acid cyclohexyl-cyclopropyl-amide | M + 1 = 466 |
| 4.6 | 2-[1-(Butane-1-sulfonyl)-piperidin-4-yl]-thiazole-4-carboxylic acid cyclohexyl-cyclopropyl-amide | M + 1 = 454.1 |
| 4.7 | 2-[1-(Propane-2-sulfonyl)-piperidin-4-yl]-thiazole-4-carboxylic acid cyclohexyl-cyclopropyl-amide | M + 1 = 454.1 |

TABLE 4-continued

| Example | Name | MS |
| --- | --- | --- |
| 4.8 | 2-[1-(Propane-1-sulfonyl)-piperidin-4-yl]-thiazole-4-carboxylic acid cyclohexyl-cyclopropyl-amide | M + 1 = 440 |
| 4.9 | 2-(1-Ethanesulfonyl-piperidin-4-yl)-thiazole-4-carboxylic acid cyclohexyl-cyclopropyl-amide | M + 1 = 426 |
| 4.10 | (Octahydro-quinolin-1-yl)-{2-[1-(thiophene-2-sulfonyl)-piperidin-4-yl]-thiazol-4-yl}-methanone | M + 1 = 480 |
| 4.11 | 2-[1-(Thiophene-2-sulfonyl)-piperidin-4-yl]-thiazole-4-carboxylic acid cyclohexyl-cyclopropyl-amide | M + 1 = 480 |
| 4.12 | 2-[1-(4-Trifluoromethoxy-benzenesulfonyl)-piperidin-4-yl]-thiazole-4-carboxylic acid cyclohexyl-cyclopropyl-amide | M + 1 = 558 |
| 4.13 | 2-[1-(4-Fluoro-benzenesulfonyl)-piperidin-4-yl]-thiazole-4-carboxylic acid cyclohexyl-cyclopropyl-amide | M + 1 = 492 |
| 4.14 | (Octahydro-quinolin-1-yl)-{2-[1-(4-trifluoromethoxy-benzenesulfonyl)-piperidin-4-yl]-thiazol-4-yl}-methanone | M + 1 = 558 |
| 4.15 | {2-[1-(4-Fluoro-benzenesulfonyl)-piperidin-4-yl]-thiazol-4-yl}-(octahydro-quinolin-1-yl)-methanone | M + 1 = 492 |
| 4.16 | {2-[1-(4-Fluoro-benzenesulfonyl)-piperidin-4-yl]-thiazol-4-yl}-(4-hydroxy-octahydro-quinolin-1-yl)-methanone | M + 1 = 508.1 |
| 4.17 | (4-Hydroxy-octahydro-quinolin-1-yl)-[2-(1-methanesulfonyl-piperidin-4-yl)-thiazol-4-yl]-methanone | M + 1 = 428.1 |
| 4.18 | 2-[1-(2-Pyridin-4-yl-ethanesulfonyl)-piperidin-4-yl]-thiazole-4-carboxylic acid cyclohexyl-cyclopropyl-amide | M + 1 = 503 |
| 4.19 | Piperidin-1-yl-{2-[1-(2-pyridin-4-yl-ethanesulfonyl)-piperidin-4-yl]-thiazol-4-yl}-methanone | M + 1 = 449 |
| 4.20 | 2-[1-(4-Methoxy-benzenesulfonyl)-piperidin-4-yl]-thiazole-4-carboxylic acid cyclohexyl-cyclopropyl-amide | M + 1 = 504 |
| 4.21 | 2-[1-(4-tert-Butyl-benzenesulfonyl)-piperidin-4-yl]-thiazole-4-carboxylic acid cyclohexyl-cyclopropyl-amide | M + 1 = 530.2 |
| 4.22 | 2-(1-Methanesulfonyl-piperidin-4-yl)-thiazole-4-carboxylic acid cyclohexyl-cyclopropyl-amide | M + 1 = 412.1 |
| 4.23 | {2-[1-(4-Methoxy-benzenesulfonyl)-piperidin-4-yl]-thiazol-4-yl}-(octahydro-quinolin-1-yl)-methanone | M + 1 = 504 |
| 4.24 | {2-[1-(4-tert-Butyl-benzenesulfonyl)-piperidin-4-yl]-thiazol-4-yl}-(octahydro-quinolin-1-yl)-methanone | M + 1 = 530.2 |
| 4.25 | [2-(1-Methanesulfonyl-piperidin-4-yl)-thiazol-4-yl]-(octahydro-quinolin-1-yl)-methanone | M + 1 = 412.1 |
| 4.26 | {2-[1-(4-Methoxy-benzenesulfonyl)-piperidin-4-yl]-thiazol-4-yl}-piperidin-1-yl-methanone | M + 1 = 450 7.83 (s, 1H) 7.61 (d, 2H) 7.11 (d, 2H) 3.53 (m, 6H) 3.27 (s, 3H) 2.99 (m, 1H) 2.38 (m, 2H) 2.01 (m, 2H) 1.53 (m, 8H) |
| 4.27 | {2-[1-(4-tert-Butyl-benzenesulfonyl)-piperidin-4-yl]-thiazol-4-yl}-piperidin-1-yl-methanone | M + 1 = 476 |
| 4.28 | [2-(1-Methanesulfonyl-piperidin-4-yl)-thiazol-4-yl]-piperidin-1-yl-methanone | M + 1 = 358.1 |
| 4.29 | 2-[1-(4-Methoxy-benzenesulfonyl)-piperidin-4-yl]-thiazole-4-carboxylic acid cyclohexyl-methyl-amide | M + 1 = 478.1 |
| 4.30 | 2-[1-(4-tert-Butyl-benzenesulfonyl)-piperidin-4-yl]-thiazole-4-carboxylic acid cyclohexyl-methyl-amide | M + 1 = 504 8.02 (s, 1H) 7.62 (m, 4H) 2.03 (m, 2H) 3.02 (m, 3H) 2.43 (s, 3H) 2.37 (m, 1H) 2.03 (m, 2H) 1.76 (m, 2H) 1.60 (m, 6H) 1.25 (s, 9H) 1.08 (m, 2H) 0.84 (m, 2H) |
| 4.31 | 2-(1-Methanesulfonyl-piperidin-4-yl)-thiazole-4-carboxylic acid cyclohexyl-methyl-amide | M + 1 = 386 |

Example 5

Method D

To 200 mg (0.6 mmol) of (Octahydro-quinolin-1-yl)-(2-piperidin-4-yl-thiazol-4-yl)-methanone in 3 ml DMF was added 165.7 mg (1.2 mmol, 2 eq) of potassium carbonate, 10 mg (0.06 mmol, 0.1 eq) of sodium iodide and 77.28 µl of 1-bromobutane. The mixture was stirred at 100° C. for 20 hrs and the reaction quenched with the addition of water. The compound was ex-tracted with AcOEt and then purified by flash chromatography to obtain 202 mg (0.5 mmol, 86%) of an oil.

The following compounds were made in a similar way as described above (table 5).

TABLE 5

| Example | Name | MS |
| --- | --- | --- |
| 5.1 | 2-(1-Cyclohexylmethyl-piperidin-4-yl)-thiazole-4-carboxylic acid cyclohexyl-cyclopropyl-amide | M + 1 = 430.2 |
| 5.2 | [2-(1-Cyclohexylmethyl-piperidin-4-yl)-thiazol-4-yl]-(octahydro-quinolin-1-yl)-methanone | M + 1 = 430.2 |
| 5.3 | 2-[1-(2-Cyclohexyl-ethyl)-piperidin-4-yl]-thiazole-4-carboxylic acid cyclohexyl-cyclopropyl-amide | M + 1 = 444.2 |
| 5.4 | 2-[1-(Tetrahydro-pyran-2-ylmethyl)-piperidin-4-yl]-thiazole-4-carboxylic acid cyclohexyl-cyclopropyl-amide | M + 1 = 432.2 |
| 5.5 | 2-(1-Cyanomethyl-piperidin-4-yl)-thiazole-4-carboxylic acid cyclohexyl-cyclopropyl-amide | M + 1 = 373.1 |

TABLE 5-continued

| Example | Name | MS |
|---|---|---|
| 5.6 | 2-(1-Carbamoylmethyl-piperidin-4-yl)-thiazole-4-carboxylic acid cyclohexyl-cyclopropyl-amide | M + 1 = 391.1 |
| 5.7 | 2-(1-Pentyl-piperidin-4-yl)-thiazole-4-carboxylic acid cyclohexyl-cyclopropyl-amide | M + 1 = 404.1 |
| 5.8 | 2-(1-Isobutyl-piperidin-4-yl)-thiazole-4-carboxylic acid cyclohexyl-cyclopropyl-amide | M + 1 = 390.2 |
| 5.9 | 2-[1-(3-Methyl-butyl)-piperidin-4-yl]-thiazole-4-carboxylic acid cyclohexyl-cyclopropyl-amide | M + 1 = 404.1 |
| 5.10 | 2-(1-Butyl-piperidin-4-yl)-thiazole-4-carboxylic acid cyclohexyl-cyclopropyl-amide | M + 1 = 390.2 |
| 5.11 | {2-[1-(2-Cyclohexyl-ethyl)-piperidin-4-yl]-thiazol-4-yl}-(octahydro-quinolin-1-yl)-methanone | M + 1 = 444.2 |
| 5.12 | (Octahydro-quinolin-1-yl)-{2-[1-(tetrahydro-pyran-2-ylmethyl)-piperidin-4-yl]-thiazol-4-yl}-methanone | M + 1 = 432.2 |
| 5.13 | {4-[4-(Octahydro-quinoline-1-carbonyl)-thiazol-2-yl]-piperidin-1-yl}-acetonitrile | M + 1 = 373.1 |
| 5.14 | 2-{4-[4-(Octahydro-quinoline-1-carbonyl)-thiazol-2-yl]-piperidin-1-yl}-acetamide | M + 1 = 391.1 |
| 5.15 | (Octahydro-quinolin-1-yl)-[2-(1-pentyl-piperidin-4-yl)-thiazol-4-yl]-methanone | M + 1 = 404.1 |
| 5.16 | [2-(1-Isobutyl-piperidin-4-yl)-thiazol-4-yl]-(octahydro-quinolin-1-yl)-methanone | M + 1 = 390.2 |
| 5.17 | {2-[1-(3-Methyl-butyl)-piperidin-4-yl]-thiazol-4-yl}-(octahydro-quinolin-1-yl)-methanone | M + 1 = 404.1 |
| 5.18 | [2-(1-Butyl-piperidin-4-yl)-thiazol-4-yl]-(octahydro-quinolin-1-yl)-methanone | M + 1 = 390.2 |

Example 6

Inhibition of 11-β-HSD-1 Enzyme Assay

Human recombinant 11-beta-hydroxysteroid dehydrogenase type 1 (11-β-HSD-1) enzyme was expressed in *E. coli*. Rat and mice liver microsome fractions were purchased from TEBU.

The 11-β-HSD-1 enzyme assay was carried out in 96 well microtiter plates in a total volume of 100 μl containing 30 mM Hepes buffer, pH 7.4 with 1 mM EDTA, substrate mixture cortisone/NADPH (200 nM/200 μM), G-6-P (1 mM) and inhibitors in serial dilutions. Reactions were initiated by addition of 10 μl 11-β-HSD-1 (3 μg) from *E. coli*, either as microsome fractions from rat and mice liver (2.5 μg). Following mixing, the plates were shaken for 150 minutes at 37° C. The reactions were terminated with 10 μl Acid-18beta Glycyrrhetinic stop solution. Determinations of Cortisol levels in 11-β-HSD-1 preparations were monitored by HTRF (HTRF Cortisol assay from Cis bio international).

Activity is expressed in % of control or concentration to inhibit 50% of the enzyme activity (IC50) (table 6).

TABLE 6

| Compound | Inhibition of human 11-β-HSD-1 IC50 (μM or nM) or % of control at 1 μM | Inhibition of mouse 11-β-HSD-1 IC50 (μM or nM) or % of control at 1 μM |
|---|---|---|
| 1.1 | 1.20 μM | 0.290 μM |
| 1.2 | 27% | — |
| 2.1 | 92 nM | 51% |
| 2.7 | 420 nM | 630 nM |
| 2.17 | 200 nM | 340 nM |
| 2.18 | 130 nM | 490 nM |
| 3.1 | 270 nM | 470 nM |
| 3.7 | 340 nM | 59 nM |
| 3.22 | 53 nM | 500 nM |
| 4.1 | 32 nM | 330 nM |
| 4.2 | 93 nM | 210 nM |
| 4.11 | 720 nM | — |
| 4.18 | 1 μM | 49% |
| 4.20 | 280 nM | 1 μM |

The invention claimed is:
1. A thiaziole compound selected from:
a) 3,3-Dimethyl-1-{4-[4-(octahydro-quinoline-1-carbonyl)-thiazol-2-yl]-piperidin-1-yl}-butan-1-one
b) (Octahydro-quinolin-1-yl)-{2-[1-(pyridine-3-carbonyl)-piperidin-4-yl]-thiazol-4-yl}-methanone
c) 2-(1-Cyclohexanecarbonyl-piperidin-4-yl)-thiazole-4-carboxylic acid cyclohexyl-cyclopropyl-amide
d) 2-(1-Cyclopentanecarbonyl-piperidin-4-yl)-thiazole-4-carboxylic acid cyclohexyl-cyclopropyl-amide
e) 2-(1-Cyclobutanecarbonyl-piperidin-4-yl)-thiazole-4-carboxylic acid cyclohexyl-cyclopropyl-amide
f) 2-(1-Cyclopropanecarbonyl-piperidin-4-yl)-thiazole-4-carboxylic acid cyclohexyl-cyclopropyl-amide
g) 2-[1-(3-Cyclopentyl-propionyl)-piperidin-4-yl]-thiazole-4-carboxylic acid cyclohexyl-cyclopropyl-amide
h) 2-[1-(2-Ethyl-butyryl)-piperidin-4-yl]-thiazole-4-carboxylic acid cyclohexyl-cyclopropyl-amide
i) 2-[1-(3,3-Dimethyl-butyryl)-piperidin-4-yl]-thiazole-4-carboxylic acid cyclohexyl-cyclopropyl-amide
j) 2-[1-(3-Methyl-butyryl)-piperidin-4-yl]-thiazole-4-carboxylic acid cyclohexyl-cyclopropyl-amide
k) 2-(1-Isobutyryl-piperidin-4-yl)-thiazole-4-carboxylic acid cyclohexyl-cyclopropyl-amide
l) 2-(1-Pentanoyl-piperidin-4-yl)-thiazole-4-carboxylic acid cyclohexyl-cyclopropyl-amide
m) 2-(1-Propionyl-piperidin-4-yl)-thiazole-4-carboxylic acid cyclohexyl-cyclopropyl-amide
n) 2-(1-Acetyl-piperidin-4-yl)-thiazole-4-carboxylic acid cyclohexyl-cyclopropyl-amide
o) 2-[1-(Pyridine-3-carbonyl)-piperidin-4-yl]-thiazole-4-carboxylic acid cyclohexyl-cyclopropyl-amide
p) 2-[1-(4-Trifluoromethoxy-benzoyl)-piperidin-4-yl]-thiazole-4-carboxylic acid cyclohexyl-cyclopropyl-amide
q) [2-(1-Cyclohexanecarbonyl-piperidin-4-yl)-thiazol-4-yl]-(octahydro-quinolin-1-yl)-methanone
r) [2-(1-Cyclopentanecarbonyl-piperidin-4-yl)-thiazol-4-yl]-(octahydro-quinolin-1-yl)-methanone
s) [2-(1-Cyclobutanecarbonyl-piperidin-4-yl)-thiazol-4-yl]-(octahydro-quinolin-1-yl)-methanone
t) [2-(1-Cyclopropanecarbonyl-piperidin-4-yl)-thiazol-4-yl]-(octahydro-quinolin-1-yl)-methanone
u) 3-Cyclopentyl-1-{4-[4-(octahydro-quinoline-1-carbonyl)-thiazol-2-yl]-piperidin-1-yl}-propan-1-one v) 2-Ethyl-1-{4-[4-(octahydro-quinoline-1-carbonyl)-thiazol-2-yl]-piperidin-1-yl}-butan-1-one
w) 3-Methyl-1-{4-[4-(octahydro-quinoline-1-carbonyl)-thiazol-2-yl]-piperidin-1-yl}-butan-1-one
x) 2-Methyl-1-{4-[4-(octahydro-quinoline-1-carbonyl)-thiazol-2-yl]-piperidin-1-yl}-propan-1-one
y) 1-{4-[4-(Octahydro-quinoline-1-carbonyl)-thiazol-2-yl]-piperidin-1-yl}-pentan-1-one
z) 1-{4-[4-(Octahydro-quinoline-1-carbonyl)-thiazol-2-yl]-piperidin-1-yl}-propan-1-one
aa) 1-{4-[4-(Octahydro-quinoline-1-carbonyl)-thiazol-2-yl]-piperidin-1-yl}-ethanone
bb) (Octahydro-quinolin-1-yl)-{2-[1-(4-trifluoromethoxy-benzoyl)-piperidin-4-yl]-thiazol-4-yl}-methanone
cc) {2-[1-(4-Fluoro-benzoyl)-piperidin-4-yl]-thiazol-4-yl}-(octahydro-quinolin-1-yl)-methanone
dd) {2-[1-(4-Fluoro-benzoyl)-piperidin-4-yl]-thiazol-4-yl}-(4-hydroxy-octahydro-quinolin-1-yl)-methanone
ee) 1-{4-[4-(4-Hydroxy-octahydro-quinoline-1-carbonyl)-thiazol-2-yl]-piperidin-1-yl}-2-(4-methoxy-phenyl)-ethanone
ff) 4-[4-(4-Hydroxy-octahydro-quinoline-1-carbonyl)-thiazol-2-yl]-piperidine-1-carboxylic acid tert-butyl ester
gg) 2-[1-(2-Phenyl-butyryl)-piperidin-4-yl]-thiazole-4-carboxylic acid cyclohexyl-cyclopropyl-amide
hh) 2-{1-[2-(4-Methoxy-phenyl)-acetyl]-piperidin-4-yl}-thiazole-4-carboxylic acid cyclohexyl-cyclopropyl-amide
ii) 2-[1-(2-Phenoxy-acetyl)-piperidin-4-yl]-thiazole-4-carboxylic acid cyclohexyl-cyclopropyl-amide
jj) 4-[4-(Cyclohexyl-cyclopropyl-carbamoyl)-thiazol-2-yl]-piperidine-1-carboxylic acid tert-butyl ester
kk) 1-{4-[4-(Octahydro-quinoline-1-carbonyl)-thiazol-2-yl]-piperidin-1-yl}-2-phenyl-butan-1-one
ll) 2-(4-Methoxy-phenyl)-1-{4-[4-(octahydro-quinoline-1-carbonyl)-thiazol-2-yl]-piperidin-1-yl}-ethanone
mm) 1-{4-[4-(Octahydro-quinoline-1-carbonyl)-thiazol-2-yl]-piperidin-1-yl}-2-phenoxy-ethanone
nn) 4-[4-(Octahydro-quinoline-1-carbonyl)-thiazol-2-yl]-piperidine-1-carboxylic acid tert-butyl ester
oo) 2-Phenyl-1-{4-[4-(piperidine-1-carbonyl)-thiazol-2-yl]-piperidin-1-yl}-butan-1-one
pp) 2-(4-Methoxy-phenyl)-1-{4-[4-(piperidine-1-carbonyl)-thiazol-2-yl]-piperidin-1-yl}-ethanone
qq) 2-Phenoxy-1-{4-[4-(piperidine-1-carbonyl)-thiazol-2-yl]-piperidin-1-yl}-ethanone
rr) 4-[4-(Piperidine-1-carbonyl)-thiazol-2-yl]-piperidine-1-carboxylic acid tert-butyl ester
ss) 2-[1-(2-Phenyl-butyryl)-piperidin-4-yl]-thiazole-4-carboxylic acid cyclohexyl-methyl-amide
tt) 2-{1-[2-(4-Methoxy-phenyl)-acetyl]-piperidin-4-yl}-thiazole-4-carboxylic acid cyclohexyl-methyl-amide
uu) 2-[1-(2-Phenoxy-acetyl)-piperidin-4-yl]-thiazole-4-carboxylic acid cyclohexyl-methyl-amide
vv) 4-[4-(Octahydro-quinoline-1-carbonyl)-thiazol-2-yl]-piperidine-1-carboxylic acid sec-butylamide
ww) 4-[4-(Octahydro-quinoline-1-carbonyl)-thiazol-2-yl]-piperidine-1-carboxylic acid tert-butylamide
xx) 4-[4-(Octahydro-quinoline-1-carbonyl)-thiazol-2-yl]-piperidine-1-carboxylic acid propylamide
yy) 4-[4-(Octahydro-quinoline-1-carbonyl)-thiazol-2-yl]-piperidine-1-carboxylic acid ethylamide
zz) 4-[4-(Octahydro-quinoline-1-carbonyl)-thiazol-2-yl]-piperidine-1-carboxylic acid cyclopentylamide
aaa) 4-[4-(Octahydro-quinoline-1-carbonyl)-thiazol-2-yl]-piperidine-1-carboxylic acid isopropylamide
bbb) 4-[4-(Octahydro-quinoline-1-carbonyl)-thiazol-2-yl]-piperidine-1-carboxylic acid pentylamide
ccc) 4-[4-(Cyclohexyl-cyclopropyl-carbamoyl)-thiazol-2-yl]-piperidine-1-carboxylic acid sec-butylamide
ddd) 4-[4-(Cyclohexyl-cyclopropyl-carbamoyl)-thiazol-2-yl]-piperidine-1-carboxylic acid tert-butylamide
eee) 4-[4-(Cyclohexyl-cyclopropyl-carbamoyl)-thiazol-2-yl]-piperidine-1-carboxylic acid propylamide
fff) 4-[4-(Cyclohexyl-cyclopropyl-carbamoyl)-thiazol-2-yl]-piperidine-1-carboxylic acid ethylamide
ggg) 4-[4-(Cyclohexyl-cyclopropyl-carbamoyl)-thiazol-2-yl]-piperidine-1-carboxylic acid cyclopentylamide
hhh) 4-[4-(Cyclohexyl-cyclopropyl-carbamoyl)-thiazol-2-yl]-piperidine-1-carboxylic acid isopropylamide
iii) 4-[4-(Cyclohexyl-cyclopropyl-carbamoyl)-thiazol-2-yl]-piperidine-1-carboxylic acid pentylamide
jjj) 4-[4-(4-Hydroxy-octahydro-quinoline-1-carbonyl)-thiazol-2-yl]-piperidine-1-carboxylic acid 4-methoxy-benzylamide
kkk) 4-[4-(4-Hydroxy-octahydro-quinoline-1-carbonyl)-thiazol-2-yl]-piperidine-1-carboxylic acid (4-butyl-phenyl)-amide
lll) 3-({4-[4-(Cyclohexyl-cyclopropyl-carbamoyl)-thiazol-2-yl]-piperidine-1-carbonyl}-amino)-propionic acid
mmm) 4-[4-(Cyclohexyl-cyclopropyl-carbamoyl)-thiazol-2-yl]-piperidine-1-carboxylic acid (4-butyl-phenyl)-amide
nnn) 4-[4-(Cyclohexyl-cyclopropyl-carbamoyl)-thiazol-2-yl]-piperidine-1-carboxylic acid 4-methoxy-benzylamide
ooo) 3-({4-[4-(Octahydro-quinoline-1-carbonyl)-thiazol-2-yl]-piperidine-1-carbonyl}-amino)-propionic acid
ppp) 4-[4-(Octahydro-quinoline-1-carbonyl)-thiazol-2-yl]-piperidine-1-carboxylic acid (4-butyl-phenyl)-amide
qqq) 4-[4-(Octahydro-quinoline-1-carbonyl)-thiazol-2-yl]-piperidine-1-carboxylic acid 4-methoxy-benzylamide
rrr) 3-({4-[4-(Piperidine-1-carbonyl)-thiazol-2-yl]-piperidine-1-carbonyl}-amino)-propionic acid
sss) 4-[4-(Piperidine-1-carbonyl)-thiazol-2-yl]-piperidine-1-carboxylic acid (4-butyl-phenyl)-amide
ttt) 4-[4-(Piperidine-1-carbonyl)-thiazol-2-yl]-piperidine-1-carboxylic acid 4-methoxy-benzyl amide
uuu) 3-({4-[4-(Cyclohexyl-methyl-carbamoyl)-thiazol-2-yl]-piperidine-1-carbonyl}-amino)-propionic acid
vvv) 4-[4-(Cyclohexyl-methyl-carbamoyl)-thiazol-2-yl]-piperidine-1-carboxylic acid (4-butyl-phenyl)-amide
www) 4-[4-(Cyclohexyl-methyl-carbamoyl)-thiazol-2-yl]-piperidine-1-carboxylic acid 4-methoxy-benzylamide
xxx) (Octahydro-quinolin-1-yl)-[2-(1-trifluoromethanesulfonyl-piperidin-4-yl)-thiazol-4-yl]-methanone
yyy) {2-[1-(Butane-1-sulfonyl)-piperidin-4-yl]-thiazol-4-yl}-(octahydro-quinolin-1-yl)-methanone
zzz) (Octahydro-quinolin-1-yl)-{2-[1-(propane-1-sulfonyl)-piperidin-4-yl]-thiazol-4-yl}-methanone
aaaa) [2-(1-Ethanesulfonyl-piperidin-4-yl)-thiazol-4-yl]-(octahydro-quinolin-1-yl)-methanone
bbbb) 2-(1-Trifluoromethanesulfonyl-piperidin-4-yl)-thiazole-4-carboxylic acid cyclohexyl-cyclopropyl-amide
cccc) 2-[1-(Butane-1-sulfonyl)-piperidin-4-yl]-thiazole-4-carboxylic acid cyclohexyl-cyclopropyl-amide dddd) 2-[1-(Propane-2-sulfonyl)-piperidin-4-yl]-thiazole-4-carboxylic acid cyclohexyl-cyclopropyl-amide
eeee) 2-[1-(Propane-1-sulfonyl)-piperidin-4-yl]-thiazole-4-carboxylic acid cyclohexyl-cyclopropyl-amide
ffff) 2-(1-Ethanesulfonyl-piperidin-4-yl)-thiazole-4-carboxylic acid cyclohexyl-cyclopropyl-amide
gggg) (Octahydro-quinolin-1-yl)-{2-[1-(thiophene-2-sulfonyl)-piperidin-4-yl]-thiazol-4-yl}-methanone
hhhh) 2-[1-(Thiophene-2-sulfonyl)-piperidin-4-yl]-thiazole-4-carboxylic acid cyclohexyl-cyclopropyl-amide
iiii) 2-[1-(4-Trifluoromethoxy-benzenesulfonyl)-piperidin-4-yl]-thiazole-4-carboxylic acid cyclohexyl-cyclopropyl-amide
jjjj) 2-[1-(4-Fluoro-benzenesulfonyl)-piperidin-4-yl]-thiazole-4-carboxylic acid cyclohexyl-cyclopropyl-amide
kkkk) (Octahydro-quinolin-1-yl)-{2-[1-(4-trifluoromethoxy-benzenesulfonyl)-piperidin-4-yl]-thiazol-4-yl}-methanone
llll) {2-[1-(4-Fluoro-benzenesulfonyl)-piperidin-4-yl]-thiazol-4-yl}-(octahydro-quinolin-1-yl)-methanone
mmmm) {2-[1-(4-Fluoro-benzenesulfonyl)-piperidin-4-yl]-thiazol-4-yl}-(4-hydroxy-octahydro-quinolin-1-yl)-methanone
nnnn) (4-Hydroxy-octahydro-quinolin-1-yl)-[2-(1-methanesulfonyl-piperidin-4-yl)-thiazol-4-yl]-methanone
oooo) 2-[1-(2-Pyridin-4-yl-ethanesulfonyl)-piperidin-4-yl]-thiazole-4-carboxylic acid cyclohexyl-cyclopropyl-amide
pppp) Piperidin-1-yl-{2-[1-(2-pyridin-4-yl-ethanesulfonyl)-piperidin-4-yl]-thiazol-4-yl}-methanone
qqqq) 2-[1-(4-Methoxy-benzenesulfonyl)-piperidin-4-yl]-thiazole-4-carboxylic acid cyclohexyl-cyclopropyl-amide
rrrr) 2-[1-(4-tert-Butyl-benzenesulfonyl)-piperidin-4-yl]-thiazole-4-carboxylic acid cyclohexyl-cyclopropyl-amide
ssss) 2-(1-Methanesulfonyl-piperidin-4-yl)-thiazole-4-carboxylic acid cyclohexyl-cyclopropyl-amide
tttt) {2-[1-(4-Methoxy-benzenesulfonyl)-piperidin-4-yl]-thiazol-4-yl}-(octahydro-quinolin-1-yl)-methanone
uuuu) {2-[1-(4-tert-Butyl-benzenesulfonyl)-piperidin-4-yl]-thiazol-4-yl}-(octahydro-quinolin-1-yl)-methanone
vvvv) [2-(1-Methanesulfonyl-piperidin-4-yl)-thiazol-4-yl]-(octahydro-quinolin-1-yl)-methanone
wwww) {2-[1-(4-Methoxy-benzenesulfonyl)-piperidin-4-yl]-thiazol-4-yl}-piperidin-1-yl-methanone
xxxx) {2-[1-(4-tert-Butyl-benzenesulfonyl)-piperidin-4-yl]-thiazol-4-yl}-piperidin-1-yl-methanone
yyyy) [2-(1-Methanesulfonyl-piperidin-4-yl)-thiazol-4-yl]-piperidin-1-yl-methanone
zzzz) 2-[1-(4-Methoxy-benzenesulfonyl)-piperidin-4-yl]-thiazole-4-carboxylic acid cyclohexyl-methyl-amide
aaaaa) 2-[1-(4-tert-Butyl-benzenesulfonyl)-piperidin-4-yl]-thiazole-4-carboxylic acid cyclohexyl-methyl-amide
bbbbb) 2-(1-Methanesulfonyl-piperidin-4-yl)-thiazole-4-carboxylic acid cyclohexyl-methyl-amide
ccccc) 2-(1-Cyclohexylmethyl-piperidin-4-yl)-thiazole-4-carboxylic acid cyclohexyl-cyclopropyl-amide
ddddd) [2-(1-Cyclohexylmethyl-piperidin-4-yl)-thiazol-4-yl]-(octahydro-quinolin-1-yl)-methanone
eeeee) 2-[1-(2-Cyclohexyl-ethyl)-piperidin-4-yl]-thiazole-4-carboxylic acid cyclohexyl-cyclopropyl-amide
fffff) 2-[1-(Tetrahydro-pyran-2-ylmethyl)-piperidin-4-yl]-thiazole-4-carboxylic acid cyclohexyl-cyclopropyl-amide
ggggg) 2-(1-Cyanomethyl-piperidin-4-yl)-thiazole-4-carboxylic acid cyclohexyl-cyclopropyl-amide
hhhhh) 2-(1-Carbamoylmethyl-piperidin-4-yl)-thiazole-4-carboxylic acid cyclohexyl-cyclopropyl-amide
iiiii) 2-(1-Pentyl-piperidin-4-yl)-thiazole-4-carboxylic acid cyclohexyl-cyclopropyl-amide
jjjjj) 2-(1-Isobutyl-piperidin-4-yl)-thiazole-4-carboxylic acid cyclohexyl-cyclopropyl-amide
kkkkk) 2-[1-(3-Methyl-butyl)-piperidin-4-yl]-thiazole-4-carboxylic acid cyclohexyl-cyclopropyl-amide
lllll) 2-(1-Butyl-piperidin-4-yl)-thiazole-4-carboxylic acid cyclohexyl-cyclopropyl-amide
mmmmm) {2-[1-(2-Cyclohexyl-ethyl)-piperidin-4-yl]-thiazol-4-yl}-(octahydro-quinolin-1-yl)-methanone
nnnnn) (Octahydro-quinolin-1-yl)-{2-[1-(tetrahydro-pyran-2-ylmethyl)-piperidin-4-yl]-thiazol-4-yl}-methanone
ooooo) {4-[4-(Octahydro-quinoline-1-carbonyl)-thiazol-2-yl]-piperidin-1-yl}-acetonitrile
ppppp) 2-{4-[4-(Octahydro-quinoline-1-carbonyl)-thiazol-2-yl]-piperidin-1-yl}-acetamide
qqqqq) (Octahydro-quinolin-1-yl)-[2-(1-pentyl-piperidin-4-yl)-thiazol-4-yl]-methanone
rrrrr) [2-(1-Isobutyl-piperidin-4-yl)-thiazol-4-yl]-(octahydro-quinolin-1-yl)-methanone
sssss) {2-[1-(3-Methyl-butyl)-piperidin-4-yl]-thiazol-4-yl}-(octahydro-quinolin-1-yl)-methanone, and
ttttt) [2-(1-Butyl-piperidin-4-yl)-thiazol-4-yl]-(octahydro-quinolin-1-yl)-methanone, and
pharmaceutically acceptable salts and stereosomers thereof.

2. A pharmaceutical composition comprising a therapeutically effective amount of at least one thiazole compound according to claim 1, and at least one physiologically acceptable excipient, auxiliary, adjuvant, diluent, carrier and/or additional pharmaceutically active substance.

3. A kit comprising:
a therapeutically effective amount of at least one thiazole compound according to claim 1; and
a therapeutically effective amount of at least one further pharmacologically active substance other than said thiazole compound.

4. A kit comprising:
a therapeutically effective amount of a pharmaceutical composition containing a thiazole compound according to claim 1, and
a therapeutically effective amount of at least one further pharmacologically active substance other than said thiazole compound.

5. A thiaziole compound according to claim 1, wherein said compound is selected from:
3,3-Dimethyl-1-{4-[4-(octahydro-quinoline-1-carbonyl)-thiazol-2-yl]-piperidin-1-yl}-butan-1-one
(Octahydro-quinolin-1-yl)-{2-[1-(pyridine-3-carbonyl)-piperidin-4-yl]-thiazol-4-yl}-methanone
3-Cyclopentyl-1-{4-[4-(octahydro-quinoline-1-carbonyl)-thiazol-2-yl]-piperidin-1-yl}-propan-1-one
2-Ethyl-1-{4-[4-(octahydro-quinoline-1-carbonyl)-thiazol-2-yl]-piperidin-1-yl}-butan-1-one
3-Methyl-1-{4-[4-(octahydro-quinoline-1-carbonyl)-thiazol-2-yl]-piperidin-1-yl}-butan-1-one
2-Methyl-1-{4-[4-(octahydro-quinoline-1-carbonyl)-thiazol-2-yl]-piperidin-1-yl}-propan-1-one
1-{4-[4-(Octahydro-quinoline-1-carbonyl)-thiazol-2-yl]-piperidin-1-yl}-pentan-1-one
1-{4-[4-(Octahydro-quinoline-1-carbonyl)-thiazol-2-yl]-piperidin-1-yl}-propan-1-one 1-{4-[4-(Octahydro-quinoline-1-carbonyl)-thiazol-2-yl]-piperidin-1-yl}-ethanone
(Octahydro-quinolin-1-yl)-{2-[1-(4-trifluoromethoxy-benzoyl)-piperidin-4-yl]-thiazol-4-yl}-methanone
1-{4-[4-(4-Hydroxy-octahydro-quinoline-1-carbonyl)-thiazol-2-yl]-piperidin-1-yl}-2-(4-methoxy-phenyl)-ethanone
4-[4-(4-Hydroxy-octahydro-quinoline-1-carbonyl)-thiazol-2-yl]-piperidine-1-carboxylic acid tert-butyl ester
1-{4-[4-(Octahydro-quinoline-1-carbonyl)-thiazol-2-yl]-piperidin-1-yl}-2-phenyl-butan-1-one
2-(4-Methoxy-phenyl)-1-{4-[4-(octahydro-quinoline-1-carbonyl)-thiazol-2-yl]-piperidin-1-yl}-ethanone
1-{4-[4-(Octahydro-quinoline-1-carbonyl)-thiazol-2-yl]-piperidin-1-yl}-2-phenoxy-ethanone
4-[4-(Octahydro-quinoline-1-carbonyl)-thiazol-2-yl]-piperidine-1-carboxylic acid tert-butyl ester
4-[4-(Octahydro-quinoline-1-carbonyl)-thiazol-2-yl]-piperidine-1-carboxylic acid sec-butylamide
4-[4-(Octahydro-quinoline-1-carbonyl)-thiazol-2-yl]-piperidine-1-carboxylic acid tert-butylamide
4-[4-(Octahydro-quinoline-1-carbonyl)-thiazol-2-yl]-piperidine-1-carboxylic acid propylamide
4-[4-(Octahydro-quinoline-1-carbonyl)-thiazol-2-yl]-piperidine-1-carboxylic acid ethylamide
4-[4-(Octahydro-quinoline-1-carbonyl)-thiazol-2-yl]-piperidine-1-carboxylic acid cyclopentylamide
4-[4-(Octahydro-quinoline-1-carbonyl)-thiazol-2-yl]-piperidine-1-carboxylic acid isopropylamide
4-[4-(Octahydro-quinoline-1-carbonyl)-thiazol-2-yl]-piperidine-1-carboxylic acid pentylamide
4-[4-(4-Hydroxy-octahydro-quinoline-1-carbonyl)-thiazol-2-yl]-piperidine-1-carboxylic acid 4-methoxy-benzylamide
4-[4-(4-Hydroxy-octahydro-quinoline-1-carbonyl)-thiazol-2-yl]-piperidine-1-carboxylic acid (4-butyl-phenyl)-amide
3-({4-[4-(Octahydro-quinoline-1-carbonyl)-thiazol-2-yl]-piperidine-1-carbonyl}-amino)-propionic acid
4-[4-(Octahydro-quinoline-1-carbonyl)-thiazol-2-yl]-piperidine-1-carboxylic acid (4-butyl-phenyl)-amide
4-[4-(Octahydro-quinoline-1-carbonyl)-thiazol-2-yl]-piperidine-1-carboxylic acid 4-methoxy-benzylamide
(Octahydro-quinolin-1-yl)-[2-(1-trifluoromethanesulfonyl-piperidin-4-yl)-thiazol-4-yl]-methanone
(Octahydro-quinolin-1-yl)-{2-[1-(propane-1-sulfonyl)-piperidin-4-yl]-thiazol-4-yl}-methanone
[2-(1-Ethanesulfonyl-piperidin-4-yl)-thiazol-4-yl]-(octahydro-quinolin-1-yl)-methanone
(Octahydro-quinolin-1-yl)-{2-[1-(thiophene-2-sulfonyl)-piperidin-4-yl]-thiazol-4-yl}-methanone
(Octahydro-quinolin-1-yl)-{2-[1-(4-trifluoromethoxy-benzenesulfonyl)-piperidin-4-yl]-thiazol-4-yl}-methanone
(Octahydro-quinolin-1-yl)-{2-[1-(tetrahydro-pyran-2-yl-methyl)-piperidin-4-yl]-thiazol-4-yl}-methanone
{4-[4-(Octahydro-quinoline-1-carbonyl)-thiazol-2-yl]-piperidin-1-yl}-acetonitrile
2-{4-[4-(Octahydro-quinoline-1-carbonyl)-thiazol-2-yl]-piperidin-1-yl}-acetamide
[2-(1-Cyclohexanecarbonyl-piperidin-4-yl)-thiazol-4-yl]-(octahydro-quinolin-1-yl)-methanone
[2-(1-Cyclopentanecarbonyl-piperidin-4-yl)-thiazol-4-yl]-(octahydro-quinolin-1-yl)-methanone
[2-(1-Cyclobutanecarbonyl-piperidin-4-yl)-thiazol-4-yl]-(octahydro-quinolin-1-yl)-methanone
[2-(1-Cyclopropanecarbonyl-piperidin-4-yl)-thiazol-4-yl]-(octahydro-quinolin-1-yl)-methanone
{2-[1-(4-Fluoro-benzoyl)-piperidin-4-yl]-thiazol-4-yl}-(octahydro-quinolin-1-yl)-methanone
{2-[1-(4-Fluoro-benzoyl)-piperidin-4-yl]-thiazol-4-yl}-(4-hydroxy-octahydro-quinolin-1-yl)-methanone
{2-[1-(Butane-1-sulfonyl)-piperidin-4-yl]-thiazol-4-yl}-(octahydro-quinolin-1-yl)-methanone
{2-[1-(4-Fluoro-benzenesulfonyl)-piperidin-4-yl]-thiazol-4-yl}-(octahydro-quinolin-1-yl)-methanone
{2-[1-(4-Fluoro-benzenesulfonyl)-piperidin-4-yl]-thiazol-4-yl}-(4-hydroxy-octahydro-quinolin-1-yl)-methanone
(4-Hydroxy-octahydro-quinolin-1-yl)-[2-(1-methanesulfonyl-piperidin-4-yl)-thiazol-4-yl]-methanone
{2-[1-(4-Methoxy-benzenesulfonyl)-piperidin-4-yl]-thiazol-4-yl}-(octahydro-quinolin-1-yl)-methanone
{2-[1-(4-tert-Butyl-benzenesulfonyl)-piperidin-4-yl]-thiazol-4-yl}-(octahydro-quinolin-1-yl)-methanone
[2-(1-Methanesulfonyl-piperidin-4-yl)-thiazol-4-yl]-(octahydro-quinolin-1-yl)-methanone
[2-(1-Cyclohexylmethyl-piperidin-4-yl)-thiazol-4-yl]-(octahydro-quinolin-1-yl)-methanone
{2-[1-(2-Cyclohexyl-ethyl)-piperidin-4-yl]-thiazol-4-yl}-(octahydro-quinolin-1-yl)-methanone
[2-(1-Isobutyl-piperidin-4-yl)-thiazol-4-yl]-(octahydro-quinolin-1-yl)-methanone
{2-[1-(3-Methyl-butyl)-piperidin-4-yl]-thiazol-4-yl}-(octahydro-quinolin-1-yl)-methanone, and
[2-(1-Butyl-piperidin-4-yl)-thiazol-4-yl]-(octahydro-quinolin-1-yl)-methanone, and
(Octahydro-quinolin-1-yl)-[2-(1-pentyl-piperidin-4-yl)-thiazol-4-yl]-methanone.

6. A thiazole compound according to claim 1, wherein said compound is selected from:
2-(1-Cyclohexanecarbonyl-piperidin-4-yl)-thiazole-4-carboxylic acid cyclohexyl-cyclopropyl-amide
2-(1-Cyclopentanecarbonyl-piperidin-4-yl)-thiazole-4-carboxylic acid cyclohexyl-cyclopropyl-amide
2-(1-Cyclobutanecarbonyl-piperidin-4-yl)-thiazole-4-carboxylic acid cyclohexyl-cyclopropyl-amide
2-(1-Cyclopropanecarbonyl-piperidin-4-yl)-thiazole-4-carboxylic acid cyclohexyl-cyclopropyl-amide
2-[1-(3-Cyclopentyl-propionyl)-piperidin-4-yl]-thiazole-4-carboxylic acid cyclohexyl-cyclopropyl-amide
2-[1-(2-Ethyl-butyryl)-piperidin-4-yl]-thiazole-4-carboxylic acid cyclohexyl-cyclopropyl-amide
2-[1-(3,3-Dimethyl-butyryl)-piperidin-4-yl]-thiazole-4-carboxylic acid cyclohexyl-cyclopropyl-amide
2-[1-(3-Methyl-butyryl)-piperidin-4-yl]-thiazole-4-carboxylic acid cyclohexyl-cyclopropyl-amide
2-(1-Isobutyryl-piperidin-4-yl)-thiazole-4-carboxylic acid cyclohexyl-cyclopropyl-amide
2-(1-Pentanoyl-piperidin-4-yl)-thiazole-4-carboxylic acid cyclohexyl-cyclopropyl-amide
2-(1-Propionyl-piperidin-4-yl)-thiazole-4-carboxylic acid cyclohexyl-cyclopropyl-amide
2-(1-Acetyl-piperidin-4-yl)-thiazole-4-carboxylic acid cyclohexyl-cyclopropyl-amide
2-[1-(Pyridine-3-carbonyl)-piperidin-4-yl]-thiazole-4-carboxylic acid cyclohexyl-cyclopropyl-amide
2-[1-(4-Trifluoromethoxy-benzoyl)-piperidin-4-yl]-thiazole-4-carboxylic acid cyclohexyl-cyclopropyl-amide
2-[1-(2-Phenyl-butyryl)-piperidin-4-yl]-thiazole-4-carboxylic acid cyclohexyl-cyclopropyl-amide 2-{1-[2-(4-Methoxy-phenyl)-acetyl]-piperidin-4-yl}-thiazole-4-carboxylic acid cyclohexyl-cyclopropyl-amide
2-[1-(2-Phenoxy-acetyl)-piperidin-4-yl]-thiazole-4-carboxylic acid cyclohexyl-cyclopropyl-amide
4-[4-(Cyclohexyl-cyclopropyl-carbamoyl)-thiazol-2-yl]-piperidine-1-carboxylic acid tert-butyl ester
4-[4-(Cyclohexyl-cyclopropyl-carbamoyl)-thiazol-2-yl]-piperidine-1-carboxylic acid sec-butylamide
4-[4-(Cyclohexyl-cyclopropyl-carbamoyl)-thiazol-2-yl]-piperidine-1-carboxylic acid tert-butylamide
4-[4-(Cyclohexyl-cyclopropyl-carbamoyl)-thiazol-2-yl]-piperidine-1-carboxylic acid propylamide
4-[4-(Cyclohexyl-cyclopropyl-carbamoyl)-thiazol-2-yl]-piperidine-1-carboxylic acid ethylamide
4-[4-(Cyclohexyl-cyclopropyl-carbamoyl)-thiazol-2-yl]-piperidine-1-carboxylic acid cyclopentylamide
4-[4-(Cyclohexyl-cyclopropyl-carbamoyl)-thiazol-2-yl]-piperidine-1-carboxylic acid isopropylamide
4-[4-(Cyclohexyl-cyclopropyl-carbamoyl)-thiazol-2-yl]-piperidine-1-carboxylic acid pentylamide
3-({4-[4-(Cyclohexyl-cyclopropyl-carbamoyl)-thiazol-2-yl]-piperidine-1-carbonyl}-amino)-propionic acid
4-[4-(Cyclohexyl-cyclopropyl-carbamoyl)-thiazol-2-yl]-piperidine-1-carboxylic acid (4-butyl-phenyl)-amide
4-[4-(Cyclohexyl-cyclopropyl-carbamoyl)-thiazol-2-yl]-piperidine-1-carboxylic acid 4-methoxy-benzylamide
2-(1-Trifluoromethanesulfonyl-piperidin-4-yl)-thiazole-4-carboxylic acid cyclohexyl-cyclopropyl-amide
2-[1-(Butane-1-sulfonyl)-piperidin-4-yl]-thiazole-4-carboxylic acid cyclohexyl-cyclopropyl-amide
2-[1-(Propane-2-sulfonyl)-piperidin-4-yl]-thiazole-4-carboxylic acid cyclohexyl-cyclopropyl-amide
2-[1-(Propane-1-sulfonyl)-piperidin-4-yl]-thiazole-4-carboxylic acid cyclohexyl-cyclopropyl-amide
2-(1-Ethanesulfonyl-piperidin-4-yl)-thiazole-4-carboxylic acid cyclohexyl-cyclopropyl-amide
2-[1-(Thiophene-2-sulfonyl)-piperidin-4-yl]-thiazole-4-carboxylic acid cyclohexyl-cyclopropyl-amide
2-[1-(4-Trifluoromethoxy-benzenesulfonyl)-piperidin-4-yl]-thiazole-4-carboxylic acid cyclohexyl-cyclopropyl-amide
2-[1-(4-Fluoro-benzenesulfonyl)-piperidin-4-yl]-thiazole-4-carboxylic acid cyclohexyl-cyclopropyl-amide
2-[1-(2-Pyridin-4-yl-ethanesulfonyl)-piperidin-4-yl]-thiazole-4-carboxylic acid cyclohexyl-cyclopropyl-amide
2-[1-(4-Methoxy-benzenesulfonyl)-piperidin-4-yl]-thiazole-4-carboxylic acid cyclohexyl-cyclopropyl-amide
2-[1-(4-tert-Butyl-benzenesulfonyl)-piperidin-4-yl]-thiazole-4-carboxylic acid cyclohexyl-cyclopropyl-amide
2-(1-Cyclohexylmethyl-piperidin-4-yl)-thiazole-4-carboxylic acid cyclohexyl-cyclopropyl-amide
2-[1-(2-Cyclohexyl-ethyl)-piperidin-4-yl]-thiazole-4-carboxylic acid cyclohexyl-cyclopropyl-amide
2-[1-(Tetrahydro-pyran-2-ylmethyl)-piperidin-4-yl]-thiazole-4-carboxylic acid cyclohexyl-cyclopropyl-amide
2-(1-Cyanomethyl-piperidin-4-yl)-thiazole-4-carboxylic acid cyclohexyl-cyclopropyl-amide
2-(1-Carbamoylmethyl-piperidin-4-yl)-thiazole-4-carboxylic acid cyclohexyl-cyclopropyl-amide
2-(1-Pentyl-piperidin-4-yl)-thiazole-4-carboxylic acid cyclohexyl-cyclopropyl-amide
2-(1-Isobutyl-piperidin-4-yl)-thiazole-4-carboxylic acid cyclohexyl-cyclopropyl-amide
2-[1-(3-Methyl-butyl)-piperidin-4-yl]-thiazole-4-carboxylic acid cyclohexyl-cyclopropyl-amide
2-(1-Butyl-piperidin-4-yl)-thiazole-4-carboxylic acid cyclohexyl-cyclopropyl-amide, and
2-(1-Methanesulfonyl-piperidin-4-yl)-thiazole-4-carboxylic acid cyclohexyl-cyclopropyl-amide.

7. A thiazole compound according to claim 1, wherein said compound is selected from:
2-[1-(2-Phenyl-butyryl)-piperidin-4-yl]-thiazole-4-carboxylic acid cyclohexyl-methyl-amide
2-{1-[2-(4-Methoxy-phenyl)-acetyl]-piperidin-4-yl}-thiazole-4-carboxylic acid cyclohexyl-methyl-amide,
2-[1-(2-Phenoxy-acetyl)-piperidin-4-yl]-thiazole-4-carboxylic acid cyclohexyl-methyl-amide
3-({4-[4-(Cyclohexyl-methyl-carbamoyl)-thiazol-2-yl]-piperidine-1-carbonyl}-amino)-propionic acid
4-[4-(Cyclohexyl-methyl-carbamoyl)-thiazol-2-yl]-piperidine-1-carboxylic acid (4-butyl-phenyl)-amide, and
4-[4-(Cyclohexyl-methyl-carbamoyl)-thiazol-2-yl]-piperidine-1-carboxylic acid 4-methoxy-benzylamide
2-[1-(4-Methoxy-benzenesulfonyl)-piperidin-4-yl]-thiazole-4-carboxylic acid cyclohexyl-methyl-amide
2-[1-(4-tert-Butyl-benzenesulfonyl)-piperidin-4-yl]-thiazole-4-carboxylic acid cyclohexyl-methyl-amide, and
2-(1-Methanesulfonyl-piperidin-4-yl)-thiazole-4-carboxylic acid cyclohexyl-methyl-amide.

8. A thiazole compound according to claim 1, wherein said compound is selected from:
2-Phenyl-1-{4-[4-(piperidine-1-carbonyl)-thiazol-2-yl]-piperidin-1-yl}-butan-1-one
2-(4-Methoxy-phenyl)-1-{4-[4-(piperidine-1-carbonyl)-thiazol-2-yl]-piperidin-1-yl}-ethanone
2-Phenoxy-1-{4-[4-(piperidine-1-carbonyl)-thiazol-2-yl]-piperidin-1-yl}-ethanone
4-[4-(Piperidine-1-carbonyl)-thiazol-2-yl]-piperidine-1-carboxylic acid tert-butyl ester
3-({4-[4-(Piperidine-1-carbonyl)-thiazol-2-yl]-piperidine-1-carbonyl}-amino)-propionic acid
4-[4-(Piperidine-1-carbonyl)-thiazol-2-yl]-piperidine-1-carboxylic acid (4-butyl-phenyl)-amide
4-[4-(Piperidine-1-carbonyl)-thiazol-2-yl]-piperidine-1-carboxylic acid 4-methoxy-benzylamide
Piperidin-1-yl-{2-[1-(2-pyridin-4-yl-ethanesulfonyl)-piperidin-4-yl]-thiazol-4-yl}-methanone
{2-[1-(4-Methoxy-benzenesulfonyl)-piperidin-4-yl]-thiazol-4-yl}-piperidin-1-yl-methanone
{2-[1-(4-tert-Butyl-benzenesulfonyl)-piperidin-4-yl]-thiazol-4-yl}-piperidin-1-yl-methanone, and
[2-(1-Methanesulfonyl-piperidin-4-yl)-thiazol-4-yl]-piperidin-1-yl-methanone.

9. A method for inhibiting 11-β-HSD-1 in a patient comprising administering to said patient a thiazole compound according to claim 1.

10. A method for inhibiting 11-β-HSD-1 in a patient comprising administering to said patient a thiazole compound according to claim 5.

11. A method for inhibiting 11-β-HSD-1 in a patient comprising administering to said patient a thiazole compound according to claim 6.

12. A method for inhibiting 11-β-HSD-1 in a patient comprising administering to said patient a thiazole compound according to claim 7.

13. A method for inhibiting 11-β-HSD-1 in a patient comprising administering to said patient a thiazole compound according to claim 8.

14. A method for treatment and/or prophylaxis of physiological and/or pathophysiological conditions, which are caused, mediated and/or propagated by high cortisol levels, comprising administering to a patient an effective amount of a compound according to claim 1.

15. A method according to claim 14, wherein the physiological and/or pathophysiological conditions are selected from metabolic syndrome, diabetes, especially non-insulin dependent diabetes mellitus, prediabetes, insulin resistance, low glucose tolerance, hyperglycemia, obesity and weight-related disorders, lipid disorders such as dyslipidemia, hyperlipidemia, hypertriglyceridemia, hypercholesterolemia, low HDL levels or high LDL levels, glaucoma, osteoporosis, glucocorticoid-mediated effects on neuronal function, such as cognitive impairment, anxiety or depression, neurodegenerative disease, immune disorders such as tuberculosis, leprosy or psoriasis, hypertension, atherosclerosis and its sequelae, vascular restenosis, cardiovascular diseases, pancreatitis, retinopathy, neuropathy and nephropathy.

16. A method according to claim 14, further comprising administering to said patient at least one additional pharmacologically active substance.

17. A method according to claim 16, wherein said compound is administered before and/or during and/or after treatment with said at least one additional pharmacologically active substance.

\* \* \* \* \*